(12) United States Patent
Herrmann et al.

(10) Patent No.: US 9,498,893 B2
(45) Date of Patent: Nov. 22, 2016

(54) SELF-RETAINING SUTURES INCLUDING TISSUE RETAINERS HAVING IMPROVED STRENGTH

(71) Applicant: Ethicon. Inc., Somerville, NJ (US)

(72) Inventors: Robert A. Herrmann, Vancouver (CA); Alexei Goraltchouk, Santa Barbara, CA (US); Lev Drubetsky, Coquitlam (CA)

(73) Assignee: Ethicon, Inc., Somerville, NJ (US)

( * ) Notice: Subject to any disclaimer, the term of this patent is extended or adjusted under 35 U.S.C. 154(b) by 114 days.

(21) Appl. No.: 14/307,787

(22) Filed: Jun. 18, 2014

(65) Prior Publication Data

US 2015/0096424 A1    Apr. 9, 2015

Related U.S. Application Data

(62) Division of application No. 12/680,176, filed as application No. PCT/US2008/077813 on Sep. 26, 2008, now Pat. No. 8,777,987.

(60) Provisional application No. 60/975,758, filed on Sep. 27, 2007.

(51) Int. Cl.
*B26D 3/08* (2006.01)
*B26D 1/25* (2006.01)
*B26D 1/00* (2006.01)
(Continued)

(52) U.S. Cl.
CPC ........... *B26D 3/08* (2013.01); *A61B 17/06166* (2013.01); *B26D 1/0006* (2013.01); *B26D 1/25* (2013.01); *B26F 3/08* (2013.01); *A61B 2017/00526* (2013.01);
(Continued)

(58) Field of Classification Search
CPC .............. A61B 17/06116; A61B 2017/06176; A61B 2017/0619; B26D 3/001; B26D 3/08; B26D 3/162; B26F 2001/3893
USPC ...................... 606/228–231; 29/7.1, 7.2, 7.3; 83/879–887
See application file for complete search history.

(56) References Cited

U.S. PATENT DOCUMENTS 709,392 A    9/1902  Brown
733,723 A    7/1903  Lukens
(Continued)

FOREIGN PATENT DOCUMENTS

BE    1014364    9/2003
CA    2309844    12/1996
(Continued)

OTHER PUBLICATIONS

US 6,447,535, (withdrawn)
(Continued)

*Primary Examiner* — Todd J Scherbel

(57) ABSTRACT

An embodiment of a suture for use in a surgical procedure applied to tissue comprises an elongated body having a first end and a second end, and a plurality of retainers arranged along a portion of the elongated body. The retainers substantially yield to motion of the elongated body within the tissue when the elongated body is drawn at the first end and resist motion of the elongated within the tissue when the elongated body is drawn at the second end. The retainers include an upper surface and a lower surface, the upper surface extending from a periphery of the elongated body and the lower surface having at least two facets.

3 Claims, 4 Drawing Sheets

(51) Int. Cl.
*A61B 17/06* (2006.01)
*B26F 3/08* (2006.01)
*A61B 17/00* (2006.01)

(52) U.S. Cl.
CPC .............. *A61B 2017/06176* (2013.01); *B26D 2001/002* (2013.01); *Y10T 83/0333* (2015.04); *Y10T 83/0341* (2015.04)

(56) References Cited

U.S. PATENT DOCUMENTS

| | | |
|---|---|---|
| 789,401 A | 5/1905 | Acheson |
| 816,026 A | 3/1906 | Meier |
| 879,758 A | 2/1908 | Foster |
| 1,142,510 A | 6/1915 | Engle |
| 1,248,825 A | 12/1917 | Dederer |
| 1,321,011 A | 11/1919 | Cottes |
| 1,558,037 A | 10/1925 | Morton |
| 1,728,316 A | 9/1929 | Von Wachenfeldt |
| 1,886,721 A | 11/1932 | O'Brien |
| 2,094,578 A | 10/1937 | Blumenthal et al. |
| 2,201,610 A | 5/1940 | Dawson, Jr. |
| 2,232,142 A | 2/1941 | Schumann |
| 2,254,620 A | 9/1941 | Miller |
| 2,347,956 A | 5/1944 | Lansing |
| 2,355,907 A | 8/1944 | Cox |
| 2,421,193 A | 5/1947 | Gardner |
| 2,452,734 A | 11/1948 | Costelow |
| 2,472,009 A | 5/1949 | Gardner |
| 2,480,271 A | 8/1949 | Sumner |
| 2,572,936 A | 10/1951 | Kulp et al. |
| 2,647,625 A | 8/1953 | Mason et al. |
| 2,684,070 A | 7/1954 | Kelsey |
| 2,736,964 A | 3/1956 | Lieberman |
| 2,779,083 A | 1/1957 | Enton |
| 2,814,296 A | 11/1957 | Everett |
| 2,817,339 A | 12/1957 | Sullivan |
| 2,866,256 A | 12/1958 | Matlin |
| 2,910,067 A | 10/1959 | White |
| 2,928,395 A | 3/1960 | Forbes et al. |
| 2,988,028 A | 6/1961 | Alcamo |
| 3,003,155 A | 10/1961 | Mielzynski et al. |
| 3,066,452 A | 12/1962 | Bott et al. |
| 3,066,673 A | 12/1962 | Bott et al. |
| 3,068,869 A | 12/1962 | Shelden et al. |
| 3,068,870 A | 12/1962 | Levin |
| 3,082,523 A | 3/1963 | Modes et al. |
| 3,123,077 A | 3/1964 | Alcamo |
| 3,166,072 A | 1/1965 | Sullivan, Jr. |
| 3,187,752 A | 6/1965 | Glick |
| 3,206,018 A | 9/1965 | Lewis et al. |
| 3,209,652 A | 10/1965 | Burgsmueller |
| 3,209,754 A | 10/1965 | Brown |
| 3,212,187 A | 10/1965 | Benedict |
| 3,214,810 A | 11/1965 | Mathison |
| 3,221,746 A | 12/1965 | Noble |
| 3,234,636 A | 2/1966 | Brown |
| 3,273,562 A | 9/1966 | Brown |
| 3,352,191 A | 11/1967 | Crawford |
| 3,378,010 A | 4/1968 | Codling |
| 3,385,299 A | 5/1968 | LeRoy |
| 3,494,006 A | 2/1970 | Brumlik |
| 3,522,637 A | 8/1970 | Brumlik |
| 3,525,340 A | 8/1970 | Gilbert |
| 3,527,223 A | 9/1970 | Shein |
| 3,545,608 A | 12/1970 | Berger et al. |
| 3,557,795 A | 1/1971 | Hirsch |
| 3,570,497 A | 3/1971 | Lemole |
| 3,586,002 A | 6/1971 | Wood |
| 3,608,095 A | 9/1971 | Barry |
| 3,608,539 A | 9/1971 | Miller |
| 3,618,447 A | 11/1971 | Goins |
| 3,646,615 A | 3/1972 | Ness |
| 3,683,926 A | 8/1972 | Suzuki |
| 3,700,433 A | 10/1972 | Duhl |
| 3,716,058 A | 2/1973 | Tanner, Jr. |
| 3,720,055 A | 3/1973 | de Mestral et al. |
| 3,748,701 A | 7/1973 | De Mestral |
| 3,762,418 A | 10/1973 | Wasson |
| 3,825,010 A | 7/1974 | McDonald |
| 3,833,972 A | 9/1974 | Brumlik |
| 3,845,641 A | 11/1974 | Waller |
| 3,847,156 A | 11/1974 | Trumble |
| 3,889,322 A | 6/1975 | Brumlik |
| 3,918,455 A | 11/1975 | Coplan |
| 3,922,455 A | 11/1975 | Brumlik |
| 3,941,164 A | 3/1976 | Musgrave |
| 3,951,261 A | 4/1976 | Mandel et al. |
| 3,977,937 A | 8/1976 | Candor |
| 3,980,177 A | 9/1976 | McGregor |
| 3,981,051 A | 9/1976 | Brumlik |
| 3,981,307 A | 9/1976 | Borysko |
| 3,985,138 A | 10/1976 | Jarvik |
| 3,985,227 A | 10/1976 | Thyen et al. |
| 3,990,144 A | 11/1976 | Schwartz |
| 4,006,747 A | 2/1977 | Kronenthal |
| 4,008,303 A | 2/1977 | Glick et al. |
| 4,024,871 A | 5/1977 | Stephenson |
| 4,027,608 A | 6/1977 | Arbuckle |
| 4,043,344 A | 8/1977 | Landi |
| 4,052,988 A | 10/1977 | Doddi et al. |
| D246,911 S | 1/1978 | Bess, Jr. et al. |
| 4,069,825 A | 1/1978 | Akiyama |
| 4,073,298 A | 2/1978 | Le Roy |
| 4,137,921 A | 2/1979 | Okuzumi et al. |
| 4,182,340 A | 1/1980 | Spencer |
| 4,186,239 A | 1/1980 | Mize et al. |
| 4,198,734 A | 4/1980 | Brumlik |
| 4,204,541 A | 5/1980 | Kapitanov |
| 4,204,542 A | 5/1980 | Bokros et al. |
| 4,259,959 A | 4/1981 | Walker |
| 4,278,374 A | 7/1981 | Wolosianski |
| 4,300,424 A | 11/1981 | Flinn |
| 4,311,002 A | 1/1982 | Hoffmann et al. |
| 4,313,448 A | 2/1982 | Stokes |
| 4,316,469 A | 2/1982 | Kapitanov |
| 4,317,451 A | 3/1982 | Cerwin et al. |
| 4,372,293 A | 2/1983 | Vijil-Rosales |
| 4,428,376 A | 1/1984 | Mericle |
| 4,430,998 A | 2/1984 | Harvey |
| 4,434,796 A | 3/1984 | Karapetian |
| 4,449,298 A | 5/1984 | Patz |
| 4,454,875 A | 6/1984 | Pratt et al. |
| 4,467,805 A | 8/1984 | Fukuda |
| 4,490,326 A | 12/1984 | Beroff et al. |
| 4,492,075 A | 1/1985 | Faure |
| 4,493,323 A | 1/1985 | Albright et al. |
| 4,505,274 A | 3/1985 | Speelman |
| 4,510,934 A | 4/1985 | Batra |
| 4,531,522 A | 7/1985 | Bedi et al. |
| 4,532,926 A | 8/1985 | O'Holla |
| 4,535,772 A | 8/1985 | Sheehan |
| 4,548,202 A | 10/1985 | Duncan |
| 4,553,544 A | 11/1985 | Nomoto et al. |
| 4,610,250 A | 9/1986 | Green |
| 4,610,251 A | 9/1986 | Kumar |
| 4,635,637 A | 1/1987 | Schreiber |
| 4,637,380 A | 1/1987 | Orejola |
| 4,653,486 A | 3/1987 | Coker |
| 4,669,473 A | 6/1987 | Richards et al. |
| 4,676,245 A | 6/1987 | Fukuda |
| 4,689,882 A | 9/1987 | Lorenz |
| 4,702,250 A | 10/1987 | Ovil et al. |
| 4,712,553 A | 12/1987 | MacGregor |
| 4,719,917 A | 1/1988 | Barrows |
| 4,741,330 A | 5/1988 | Hayhurst |
| 4,750,910 A | 6/1988 | Takayanagi et al. |
| 4,751,621 A | 6/1988 | Jenkins |
| 4,776,337 A | 10/1988 | Palmaz |
| 4,813,537 A | 3/1989 | Okuhara et al. |
| 4,832,025 A | 5/1989 | Coates |
| 4,841,960 A | 6/1989 | Garner |
| 4,865,026 A | 9/1989 | Barrett |
| 4,873,976 A | 10/1989 | Schreiber |

(56) References Cited

U.S. PATENT DOCUMENTS

| | | |
|---|---|---|
| 4,887,601 A | 12/1989 | Richards |
| 4,895,148 A | 1/1990 | Bays et al. |
| 4,898,156 A | 2/1990 | Gatturna et al. |
| 4,899,743 A | 2/1990 | Nicholson et al. |
| 4,900,605 A | 2/1990 | Thorgersen et al. |
| 4,905,367 A | 3/1990 | Pinchuck et al. |
| 4,930,945 A | 6/1990 | Arai et al. |
| 4,932,962 A | 6/1990 | Yoon et al. |
| 4,946,468 A | 8/1990 | Li |
| 4,948,444 A | 8/1990 | Schultz et al. |
| 4,950,258 A | 8/1990 | Kawai et al. |
| 4,950,285 A | 8/1990 | Wilk |
| 4,968,315 A | 11/1990 | Gatturna |
| 4,976,715 A | 12/1990 | Bays et al. |
| 4,979,956 A | 12/1990 | Silvestrini et al. |
| 4,981,149 A | 1/1991 | Yoon |
| 4,994,073 A | 2/1991 | Green |
| 4,994,084 A | 2/1991 | Brennan |
| 4,997,439 A | 3/1991 | Chen |
| 5,002,550 A | 3/1991 | Li |
| 5,002,562 A | 3/1991 | Oberlander |
| 5,007,921 A | 4/1991 | Brown |
| 5,007,922 A | 4/1991 | Chen et al. |
| 5,026,390 A | 6/1991 | Brown |
| 5,037,422 A | 8/1991 | Hayhurst et al. |
| 5,037,433 A | 8/1991 | Wilk et al. |
| 5,041,129 A | 8/1991 | Hayhurst et al. |
| 5,046,513 A | 9/1991 | Gatturna et al. |
| 5,047,047 A | 9/1991 | Yoon |
| 5,053,047 A | 10/1991 | Yoon |
| 5,084,063 A | 1/1992 | Korthoff |
| 5,089,010 A | 2/1992 | Korthoff |
| 5,101,968 A | 4/1992 | Henderson et al. |
| 5,102,418 A | 4/1992 | Granger et al. |
| 5,102,421 A | 4/1992 | Anpach, Jr. |
| 5,103,073 A | 4/1992 | Danilov et al. |
| 5,112,344 A | 5/1992 | Petros |
| 5,123,911 A | 6/1992 | Granger et al. |
| 5,123,913 A | 6/1992 | Wilk et al. |
| 5,123,919 A | 6/1992 | Sauter et al. |
| 5,127,413 A | 7/1992 | Ebert |
| 5,133,738 A | 7/1992 | Korthoff et al. |
| 5,141,520 A | 8/1992 | Goble et al. |
| 5,147,382 A | 9/1992 | Gertzman et al. |
| 5,156,615 A | 10/1992 | Korthoff et al. |
| 5,156,788 A | 10/1992 | Chesterfield et al. |
| 5,176,692 A | 1/1993 | Wilk et al. |
| 5,179,964 A | 1/1993 | Cook |
| 5,192,274 A | 3/1993 | Bierman |
| 5,192,302 A | 3/1993 | Kensey et al. |
| 5,192,303 A | 3/1993 | Gatturna et al. |
| 5,197,597 A | 3/1993 | Leary et al. |
| 5,201,326 A | 4/1993 | Kubicki et al. |
| 5,207,679 A | 5/1993 | Li |
| 5,207,694 A | 5/1993 | Broome |
| 5,217,486 A | 6/1993 | Rice et al. |
| 5,217,494 A | 6/1993 | Coggins et al. |
| 5,222,508 A | 6/1993 | Contarini |
| 5,222,976 A | 6/1993 | Yoon |
| 5,224,946 A | 7/1993 | Hayhurst et al. |
| 5,234,006 A | 8/1993 | Eaton et al. |
| 5,242,457 A | 9/1993 | Akopov et al. |
| 5,246,441 A | 9/1993 | Ross et al. |
| 5,249,673 A | 10/1993 | Sinn |
| 5,258,013 A | 11/1993 | Granger et al. |
| 5,259,846 A | 11/1993 | Granger et al. |
| 5,263,973 A | 11/1993 | Cook |
| 5,269,783 A | 12/1993 | Sander |
| 5,282,832 A | 2/1994 | Toso et al. |
| 5,292,326 A | 3/1994 | Green |
| 5,306,288 A | 4/1994 | Granger et al. |
| 5,306,290 A | 4/1994 | Martins et al. |
| 5,320,629 A | 6/1994 | Noda et al. |
| 5,330,488 A | 7/1994 | Goldrath |
| 5,330,503 A | 7/1994 | Yoon |
| 5,336,239 A | 8/1994 | Gimpelson |
| 5,341,922 A | 8/1994 | Cerwin et al. |
| 5,342,376 A | 8/1994 | Ruff |
| 5,342,395 A | 8/1994 | Jarrett et al. |
| 5,350,385 A | 9/1994 | Christy |
| 5,352,515 A | 10/1994 | Jarrett et al. |
| 5,354,271 A | 10/1994 | Voda |
| 5,354,298 A | 10/1994 | Lee et al. |
| 5,358,511 A | 10/1994 | Gatturna et al. |
| 5,363,556 A | 11/1994 | Banholzer et al. |
| 5,372,146 A | 12/1994 | Branch |
| 5,374,268 A | 12/1994 | Sander |
| 5,374,278 A | 12/1994 | Chesterfield et al. |
| 5,380,334 A | 1/1995 | Torrie et al. |
| 5,387,383 A | 2/1995 | Collier et al. |
| 5,391,173 A | 2/1995 | Wilk |
| 5,395,126 A | 3/1995 | Tresslar |
| 5,403,346 A | 4/1995 | Loeser |
| 5,411,523 A | 5/1995 | Goble |
| 5,414,988 A | 5/1995 | DiPalma et al. |
| 5,417,691 A | 5/1995 | Hayhurst |
| 5,425,746 A | 6/1995 | Proto et al. |
| 5,425,747 A | 6/1995 | Brotz |
| 5,437,680 A | 8/1995 | Yoon et al. |
| 5,450,860 A | 9/1995 | O'Connor |
| 5,451,461 A | 9/1995 | Broyer |
| 5,454,834 A | 10/1995 | Boebel et al. |
| 5,462,561 A | 10/1995 | Voda |
| 5,464,426 A | 11/1995 | Bonutti |
| 5,464,427 A | 11/1995 | Curtis et al. |
| 5,466,241 A | 11/1995 | Leroy et al. |
| 5,472,452 A | 12/1995 | Trott |
| 5,478,353 A | 12/1995 | Yoon |
| 5,480,403 A | 1/1996 | Lee et al. |
| 5,480,411 A | 1/1996 | Liu et al. |
| 5,484,451 A | 1/1996 | Akopov et al. |
| 5,486,197 A | 1/1996 | Le et al. |
| 5,494,154 A | 2/1996 | Ainsworth et al. |
| 5,500,000 A | 3/1996 | Feagin et al. |
| 5,500,991 A | 3/1996 | Demarest et al. |
| 5,520,084 A | 5/1996 | Chesterfield et al. |
| 5,520,691 A | 5/1996 | Branch |
| 5,522,845 A | 6/1996 | Wenstrom, Jr. |
| 5,527,342 A | 6/1996 | Pietrzak et al. |
| 5,531,760 A | 7/1996 | Alwafaie |
| 5,531,761 A | 7/1996 | Yoon |
| 5,531,790 A | 7/1996 | Frechet et al. |
| 5,533,982 A | 7/1996 | Rizk et al. |
| 5,536,582 A | 7/1996 | Prasad et al. |
| 5,540,705 A | 7/1996 | Meade et al. |
| 5,540,718 A | 7/1996 | Bartlett |
| 5,545,148 A | 8/1996 | Wurster |
| 5,546,957 A | 8/1996 | Heske |
| 5,549,631 A | 8/1996 | Bonutti |
| 5,554,171 A | 9/1996 | Gatturna et al. |
| 5,566,822 A | 10/1996 | Scanlon |
| 5,569,272 A | 10/1996 | Reed et al. |
| 5,571,139 A | 11/1996 | Jenkins, Jr. |
| 5,571,175 A | 11/1996 | Vanney et al. |
| 5,571,216 A | 11/1996 | Anderson |
| 5,573,543 A | 11/1996 | Akopov et al. |
| 5,584,859 A | 12/1996 | Brotz |
| 5,593,424 A | 1/1997 | Northrup, III et al. |
| 5,601,557 A | 2/1997 | Hayhurst |
| 5,626,590 A | 5/1997 | Wilk |
| 5,626,611 A | 5/1997 | Liu et al. |
| 5,632,753 A | 5/1997 | Loeser |
| 5,643,288 A | 7/1997 | Thompson |
| 5,643,295 A | 7/1997 | Yoon |
| 5,643,319 A | 7/1997 | Green et al. |
| 5,645,568 A | 7/1997 | Chervitz et al. |
| 5,647,874 A | 7/1997 | Hayhurst |
| 5,649,939 A | 7/1997 | Reddick |
| 5,653,716 A | 8/1997 | Malo et al. |
| 5,662,654 A | 9/1997 | Thompson |
| 5,662,714 A | 9/1997 | Charvin et al. |
| 5,669,935 A | 9/1997 | Rosenman et al. |
| 5,676,675 A | 10/1997 | Grice |
| D386,583 S | 11/1997 | Ferragamo et al. |

(56) References Cited

U.S. PATENT DOCUMENTS

| | | |
|---|---|---|
| 5,683,417 A | 11/1997 | Cooper |
| D387,161 S | 12/1997 | Ferragamo et al. |
| 5,695,879 A | 12/1997 | Goldmann et al. |
| 5,697,976 A | 12/1997 | Chesterfield et al. |
| 5,702,397 A | 12/1997 | Goble et al. |
| 5,702,462 A | 12/1997 | Oberlander |
| 5,709,692 A | 1/1998 | Mollenauer et al. |
| 5,716,358 A | 2/1998 | Ochoa et al. |
| 5,716,376 A | 2/1998 | Roby et al. |
| 5,722,991 A | 3/1998 | Colligan |
| 5,723,008 A | 3/1998 | Gordon |
| 5,725,557 A | 3/1998 | Gatturna et al. |
| 5,728,114 A | 3/1998 | Evans et al. |
| 5,731,855 A | 3/1998 | Koyama et al. |
| 5,741,277 A | 4/1998 | Gordon et al. |
| 5,744,151 A | 4/1998 | Capelli |
| 5,763,411 A | 6/1998 | Edwardson et al. |
| 5,765,560 A | 6/1998 | Verkerke et al. |
| 5,766,246 A | 6/1998 | Mulhauser et al. |
| 5,779,719 A | 7/1998 | Klein et al. |
| 5,782,864 A | 7/1998 | Lizardi |
| 5,807,403 A | 9/1998 | Beyar et al. |
| 5,807,406 A | 9/1998 | Brauker et al. |
| 5,810,853 A | 9/1998 | Yoon |
| 5,814,051 A | 9/1998 | Wenstrom, Jr. |
| 5,843,087 A | 12/1998 | Jensen et al. |
| 5,843,178 A | 12/1998 | Vanney et al. |
| 5,855,619 A | 1/1999 | Caplan et al. |
| 5,863,360 A | 1/1999 | Wood et al. |
| 5,887,594 A | 3/1999 | LoCicero, III |
| 5,891,166 A | 4/1999 | Schervinsky |
| 5,893,856 A | 4/1999 | Jacob et al. |
| 5,895,395 A | 4/1999 | Yeung |
| 5,895,413 A | 4/1999 | Nordstrom |
| 5,897,572 A | 4/1999 | Schulsinger et al. |
| 5,899,911 A | 5/1999 | Carter |
| 5,916,224 A | 6/1999 | Esplin |
| 5,919,234 A | 7/1999 | Lemperle et al. |
| 5,921,982 A | 7/1999 | Lesh et al. |
| 5,925,078 A | 7/1999 | Anderson |
| 5,931,855 A | 8/1999 | Buncke |
| 5,935,138 A | 8/1999 | McJames, II et al. |
| 5,938,668 A | 8/1999 | Scirica et al. |
| 5,950,633 A | 9/1999 | Lynch et al. |
| 5,954,747 A | 9/1999 | Clark |
| 5,964,765 A | 10/1999 | Fenton, Jr. et al. |
| 5,964,783 A | 10/1999 | Grafton et al. |
| 5,968,097 A | 10/1999 | Frechet et al. |
| 5,972,024 A | 10/1999 | Northrup, III et al. |
| 5,984,933 A | 11/1999 | Yoon |
| 5,993,459 A | 11/1999 | Larsen et al. |
| 5,997,554 A | 12/1999 | Thompson |
| 6,001,111 A | 12/1999 | Sepetka et al. |
| 6,012,216 A | 1/2000 | Esteves et al. |
| 6,015,410 A | 1/2000 | Tormala et al. |
| 6,024,757 A | 2/2000 | Haase et al. |
| 6,027,523 A | 2/2000 | Schmieding |
| 6,039,741 A | 3/2000 | Meislin |
| 6,042,583 A | 3/2000 | Thompson et al. |
| 6,045,571 A | 4/2000 | Hill et al. |
| 6,056,778 A | 5/2000 | Grafton et al. |
| 6,063,105 A | 5/2000 | Totakura |
| 6,071,292 A | 6/2000 | Makower et al. |
| 6,074,419 A | 6/2000 | Healy et al. |
| 6,076,255 A | 6/2000 | Shikakubo et al. |
| 6,083,244 A | 7/2000 | Lubbers et al. |
| 6,102,947 A | 8/2000 | Gordon |
| 6,106,544 A | 8/2000 | Brazeau |
| 6,106,545 A | 8/2000 | Egan |
| 6,110,484 A | 8/2000 | Sierra |
| D433,753 S | 11/2000 | Weiss |
| 6,146,406 A | 11/2000 | Shluzas et al. |
| 6,146,407 A | 11/2000 | Krebs |
| 6,149,660 A | 11/2000 | Laufer et al. |
| 6,159,234 A | 12/2000 | Bonutti et al. |
| 6,160,084 A | 12/2000 | Langer et al. |
| 6,163,948 A | 12/2000 | Esteves et al. |
| 6,165,203 A | 12/2000 | Krebs |
| 6,168,633 B1 | 1/2001 | Shoher et al. |
| 6,174,324 B1 | 1/2001 | Egan et al. |
| 6,183,499 B1 | 2/2001 | Fischer et al. |
| 6,187,095 B1 | 2/2001 | Labrecque et al. |
| 6,203,565 B1 | 3/2001 | Bonutti et al. |
| 6,206,908 B1 | 3/2001 | Roby |
| 6,231,911 B1 | 5/2001 | Steinback et al. |
| 6,235,869 B1 | 5/2001 | Roby et al. |
| 6,241,747 B1 | 6/2001 | Ruff |
| 6,251,143 B1 | 6/2001 | Schwartz et al. |
| 6,264,675 B1 | 7/2001 | Brotz |
| 6,267,772 B1 | 7/2001 | Mulhauser et al. |
| 6,270,517 B1 | 8/2001 | Brotz |
| 6,315,788 B1 | 11/2001 | Roby |
| 6,319,231 B1 | 11/2001 | Andrulitis |
| 6,334,865 B1 | 1/2002 | Redmond et al. |
| 6,383,201 B1 | 5/2002 | Dong |
| 6,387,363 B1 | 5/2002 | Gruskin |
| 6,388,043 B1 | 5/2002 | Langer et al. |
| 6,395,029 B1 | 5/2002 | Levy |
| D462,766 S | 9/2002 | Jacobs et al. |
| 6,443,962 B1 | 9/2002 | Gaber |
| 6,463,719 B2 | 10/2002 | Dey et al. |
| 6,471,715 B1 | 10/2002 | Weiss |
| 6,478,809 B1 | 11/2002 | Brotz |
| 6,485,503 B2 | 11/2002 | Jacobs et al. |
| 6,491,701 B2 | 12/2002 | Tierney et al. |
| 6,491,714 B1 | 12/2002 | Bennett |
| 6,494,898 B1 | 12/2002 | Roby et al. |
| 6,495,127 B1 | 12/2002 | Wallace et al. |
| RE37,963 E | 1/2003 | Thal |
| 6,506,190 B1 | 1/2003 | Walshe |
| 6,506,197 B1 | 1/2003 | Rollero et al. |
| 6,511,488 B1 | 1/2003 | Marshall et al. |
| 6,514,265 B2 | 2/2003 | Ho et al. |
| 6,527,795 B1 | 3/2003 | Lizardi |
| 6,548,002 B2 | 4/2003 | Gresser et al. |
| 6,548,569 B1 | 4/2003 | Williams et al. |
| 6,551,343 B1 | 4/2003 | Tormala et al. |
| 6,554,802 B1 | 4/2003 | Pearson et al. |
| 6,565,597 B1 | 5/2003 | Fearnot et al. |
| 6,592,609 B1 | 7/2003 | Bonutti |
| 6,596,296 B1 | 7/2003 | Nelson et al. |
| 6,599,310 B2 | 7/2003 | Leung et al. |
| 6,607,541 B1 | 8/2003 | Gardiner et al. |
| 6,610,078 B1 | 8/2003 | Bru-Magniez et al. |
| 6,613,059 B2 | 9/2003 | Schaller et al. |
| 6,613,254 B1 | 9/2003 | Shiffer |
| 6,616,982 B2 | 9/2003 | Merrill et al. |
| 6,623,492 B1 | 9/2003 | Berube et al. |
| 6,626,930 B1 | 9/2003 | Allen et al. |
| 6,632,245 B2 | 10/2003 | Kim |
| 6,641,592 B1 | 11/2003 | Sauer et al. |
| 6,641,593 B1 | 11/2003 | Schaller et al. |
| 6,645,226 B1 | 11/2003 | Jacobs et al. |
| 6,645,227 B2 | 11/2003 | Fallin et al. |
| 6,648,921 B2 | 11/2003 | Anderson et al. |
| 6,656,182 B1 | 12/2003 | Hayhurst |
| 6,689,153 B1 | 2/2004 | Skiba |
| 6,689,166 B2 | 2/2004 | Laurencin et al. |
| 6,692,761 B2 | 2/2004 | Mahmood et al. |
| 6,702,844 B1 | 3/2004 | Lazarus |
| 6,712,830 B2 | 3/2004 | Esplin |
| 6,712,859 B2 | 3/2004 | Rousseau et al. |
| 6,716,234 B2 | 4/2004 | Grafton et al. |
| 6,720,402 B2 | 4/2004 | Langer et al. |
| 6,726,705 B2 | 4/2004 | Peterson et al. |
| 6,746,443 B1 | 6/2004 | Morley et al. |
| 6,746,458 B1 | 6/2004 | Cloud |
| 6,749,616 B1 | 6/2004 | Nath |
| 6,773,450 B2 | 8/2004 | Leung et al. |
| 6,783,554 B2 | 8/2004 | Amara et al. |
| 6,814,748 B1 | 11/2004 | Baker et al. |
| 6,818,010 B2 | 11/2004 | Eichhorn et al. |
| 6,838,493 B2 | 1/2005 | Williams et al. |
| 6,848,152 B2 | 2/2005 | Genova et al. |

(56) References Cited

U.S. PATENT DOCUMENTS

| | | | |
|---|---|---|---|
| 6,852,825 B2 | 2/2005 | Ledlein et al. |
| 6,858,222 B2 | 2/2005 | Nelson et al. |
| 6,860,891 B2 | 3/2005 | Schulze |
| 6,860,901 B1 | 3/2005 | Baker et al. |
| 6,867,248 B1 | 3/2005 | Martin et al. |
| 6,877,934 B2 | 4/2005 | Gainer |
| 6,881,766 B2 | 4/2005 | Hain |
| 6,893,452 B2 | 5/2005 | Jacobs |
| 6,905,484 B2 | 6/2005 | Buckman et al. |
| 6,911,035 B1 | 6/2005 | Blomme |
| 6,911,037 B2 | 6/2005 | Gainor et al. |
| 6,913,607 B2 | 7/2005 | Ainsworth et al. |
| 6,921,811 B2 | 7/2005 | Zamora et al. |
| 6,923,819 B2 | 8/2005 | Meade et al. |
| 6,945,021 B2 | 9/2005 | Michel |
| 6,945,980 B2 | 9/2005 | Nguyen et al. |
| 6,960,221 B2 | 11/2005 | Ho et al. |
| 6,960,233 B1 | 11/2005 | Berg et al. |
| 6,974,450 B2 | 12/2005 | Weber et al. |
| 6,981,983 B1 | 1/2006 | Rosenblatt et al. |
| 6,984,241 B2 | 1/2006 | Lubbers et al. |
| 6,986,780 B2 | 1/2006 | Rudnick et al. |
| 6,991,643 B2 | 1/2006 | Saadat |
| 6,996,880 B2 | 2/2006 | Kurtz, Jr. |
| 7,021,316 B2 | 4/2006 | Leiboff |
| 7,029,490 B2 | 4/2006 | Grafton et al. |
| 7,033,379 B2 | 4/2006 | Peterson |
| 7,033,603 B2 | 4/2006 | Nelson et al. |
| 7,037,175 B1 * | 5/2006 | Spiro .............. A61B 17/3211 |
| | | | 451/45 |
| 7,037,984 B2 | 5/2006 | Ledlein et al. |
| 7,048,748 B1 | 5/2006 | Ustuner |
| 7,056,331 B2 | 6/2006 | Kaplan et al. |
| 7,056,333 B2 | 6/2006 | Walshe |
| 7,057,135 B2 | 6/2006 | Li |
| 7,070,610 B2 | 7/2006 | Im et al. |
| 7,081,135 B2 | 7/2006 | Smith et al. |
| 7,083,637 B1 | 8/2006 | Tannhauser |
| 7,083,648 B2 | 8/2006 | Yu et al. |
| 7,107,090 B2 | 9/2006 | Salisbury, Jr. et al. |
| 7,112,214 B2 | 9/2006 | Peterson et al. |
| 7,125,403 B2 | 10/2006 | Julian et al. |
| 7,125,413 B2 | 10/2006 | Grigoryants et al. |
| D532,107 S | 11/2006 | Peterson et al. |
| 7,138,441 B1 | 11/2006 | Zhang |
| 7,141,302 B2 | 11/2006 | Mueller et al. |
| 7,144,401 B2 | 12/2006 | Yamamoto et al. |
| 7,144,412 B2 | 12/2006 | Wolf et al. |
| 7,144,415 B2 | 12/2006 | DelRio et al. |
| 7,150,757 B2 | 12/2006 | Fallin et al. |
| 7,156,858 B2 | 1/2007 | Shuldt-Hempe et al. |
| 7,156,862 B2 | 1/2007 | Jacobs et al. |
| 7,160,312 B2 | 1/2007 | Saadat |
| 7,166,570 B2 | 1/2007 | Hunter et al. |
| 7,172,595 B1 | 2/2007 | Goble |
| 7,172,615 B2 | 2/2007 | Morriss et al. |
| 7,186,262 B2 | 3/2007 | Saadat |
| 7,195,634 B2 | 3/2007 | Schmieding et al. |
| 7,211,088 B2 | 5/2007 | Grafton et |
| 7,214,230 B2 | 5/2007 | Brock et al. |
| 7,217,744 B2 | 5/2007 | Lendlein et al. |
| 7,225,512 B2 | 6/2007 | Genova et al. |
| 7,226,468 B2 | 6/2007 | Ruff |
| 7,232,447 B2 | 6/2007 | Gellman et al. |
| 7,244,270 B2 | 7/2007 | Lesh et al. |
| 7,279,612 B1 | 10/2007 | Heaton et al. |
| 7,297,142 B2 | 11/2007 | Brock |
| 7,322,105 B2 | 1/2008 | Lewis |
| 7,329,271 B2 | 2/2008 | Koyfman et al. |
| 7,371,253 B2 | 5/2008 | Leung et al. |
| 7,513,904 B2 | 4/2009 | Sulamanidze et al. |
| 7,582,105 B2 | 9/2009 | Kolster |
| 7,601,164 B2 | 10/2009 | Wu |
| 7,624,487 B2 | 12/2009 | Trull et al. |
| 7,645,293 B2 | 1/2010 | Martinek et al. |
| 7,806,908 B2 | 10/2010 | Ruff |
| 7,845,356 B2 | 12/2010 | Paraschac et al. |
| 7,850,894 B2 | 12/2010 | Lindh, Sr. |
| 7,857,829 B2 | 12/2010 | Kaplan et al. |
| 7,879,072 B2 | 2/2011 | Bonutti et al. |
| 7,913,365 B2 | 3/2011 | Genova et al. |
| 7,919,112 B2 | 4/2011 | Pathak et al. |
| 7,996,967 B2 | 8/2011 | Genova et al. |
| 8,032,996 B2 * | 10/2011 | Trull .............. A61B 17/06166 |
| | | | 29/7.1 |
| 8,100,940 B2 | 1/2012 | Leung et al. |
| 8,118,834 B1 | 2/2012 | Goraltchouk et al. |
| 8,216,273 B1 | 7/2012 | Goraltchouk et al. |
| 8,226,684 B2 | 7/2012 | Nawrocki et al. |
| 8,246,652 B2 | 8/2012 | Ruff |
| 8,273,105 B2 | 9/2012 | Cohen et al. |
| 8,308,761 B2 | 11/2012 | Brailovski et al. |
| 8,615,856 B1 | 12/2013 | Gelbart |
| 8,641,732 B1 | 2/2014 | Goraltchouk et al. |
| 9,023,081 B2 | 5/2015 | Maiorino et al. |
| 9,038,688 B2 | 5/2015 | Maiorino et al. |
| 2001/0011187 A1 | 8/2001 | Pavcnik et al. |
| 2001/0018592 A1 | 8/2001 | Schaller et al. |
| 2001/0018599 A1 | 8/2001 | D'Aversa et al. |
| 2001/0039450 A1 | 11/2001 | Pavcnik et al. |
| 2001/0044637 A1 | 11/2001 | Jacobs et al. |
| 2001/0051807 A1 | 12/2001 | Grafton |
| 2001/0051815 A1 | 12/2001 | Esplin |
| 2002/0007218 A1 | 1/2002 | Cauthen |
| 2002/0022861 A1 | 2/2002 | Jacobs et al. |
| 2002/0029011 A1 | 3/2002 | Dyer |
| 2002/0029066 A1 | 3/2002 | Foerster |
| 2002/0069617 A1 | 6/2002 | Dey et al. |
| 2002/0077448 A1 | 6/2002 | Antal et al. |
| 2002/0077631 A1 | 6/2002 | Lubbers et al. |
| 2002/0095164 A1 | 7/2002 | Andreas et al. |
| 2002/0099394 A1 | 7/2002 | Houser et al. |
| 2002/0111641 A1 | 8/2002 | Peterson et al. |
| 2002/0111688 A1 | 8/2002 | Cauthen |
| 2002/0138009 A1 | 9/2002 | Brockway et al. |
| 2002/0151932 A1 | 10/2002 | Bryant et al. |
| 2002/0151980 A1 | 10/2002 | Cauthen |
| 2002/0161168 A1 | 10/2002 | Shalaby et al. |
| 2002/0165555 A1 | 11/2002 | Stein et al. |
| 2002/0173807 A1 | 11/2002 | Jacobs |
| 2002/0173822 A1 | 11/2002 | Justin et al. |
| 2002/0179718 A1 | 12/2002 | Murokh et al. |
| 2002/0198544 A1 | 12/2002 | Uflacker |
| 2003/0014077 A1 | 1/2003 | Leung et al. |
| 2003/0040795 A1 | 2/2003 | Elson et al. |
| 2003/0041426 A1 | 3/2003 | Genova et al. |
| 2003/0065360 A1 | 4/2003 | Jacobs et al. |
| 2003/0065402 A1 | 4/2003 | Anderson et al. |
| 2003/0069602 A1 | 4/2003 | Jacobs et al. |
| 2003/0074021 A1 | 4/2003 | Morriss et al. |
| 2003/0074023 A1 | 4/2003 | Kaplan et al. |
| 2003/0078604 A1 | 4/2003 | Walshe |
| 2003/0088270 A1 | 5/2003 | Lubbers et al. |
| 2003/0097150 A1 | 5/2003 | Fallin et al. |
| 2003/0105489 A1 | 6/2003 | Eichhorn et al. |
| 2003/0149447 A1 | 8/2003 | Morency |
| 2003/0158604 A1 | 8/2003 | Cauthen, III et al. |
| 2003/0167072 A1 | 9/2003 | Oberlander |
| 2003/0199923 A1 | 10/2003 | Khairkhahan et al. |
| 2003/0203003 A1 | 10/2003 | Nelson et al. |
| 2003/0204193 A1 | 10/2003 | Gabriel et al. |
| 2003/0204195 A1 | 10/2003 | Keane et al. |
| 2003/0225424 A1 | 12/2003 | Benderev |
| 2003/0229361 A1 | 12/2003 | Jackson |
| 2003/0236550 A1 | 12/2003 | Peterson et al. |
| 2003/0236551 A1 | 12/2003 | Peterson |
| 2004/0006353 A1 | 1/2004 | Bosley, Jr. et al. |
| 2004/0010275 A1 | 1/2004 | Jacobs et al. |
| 2004/0010276 A1 | 1/2004 | Jacobs et al. |
| 2004/0015187 A1 | 1/2004 | Lendlein et al. |
| 2004/0024169 A1 | 2/2004 | Shalaby et al. |
| 2004/0024420 A1 | 2/2004 | Lubbers et al. |
| 2004/0028655 A1 | 2/2004 | Nelson et al. |
| 2004/0030354 A1 | 2/2004 | Leung et al. |

(56) References Cited

U.S. PATENT DOCUMENTS

| | | |
|---|---|---|
| 2004/0039415 A1 | 2/2004 | Zamierowski |
| 2004/0049224 A1 | 3/2004 | Buehlmann et al. |
| 2004/0059370 A1 | 3/2004 | Greene, Jr. et al. |
| 2004/0059377 A1 | 3/2004 | Peterson et al. |
| 2004/0059378 A1 | 3/2004 | Peterson et al. |
| 2004/0060409 A1 | 4/2004 | Leung et al. |
| 2004/0060410 A1 | 4/2004 | Leung et al. |
| 2004/0068293 A1 | 4/2004 | Scalzo et al. |
| 2004/0068294 A1 | 4/2004 | Scalzo et al. |
| 2004/0088003 A1 | 5/2004 | Leung et al. |
| 2004/0093023 A1 | 5/2004 | Allen et al. |
| 2004/0093028 A1 | 5/2004 | Ruff |
| 2004/0098051 A1 | 5/2004 | Fallin et al. |
| 2004/0106949 A1 | 6/2004 | Cohn et al. |
| 2004/0116620 A1 | 6/2004 | Shalaby et al. |
| 2004/0138683 A1 | 7/2004 | Shelton et al. |
| 2004/0153153 A1 | 8/2004 | Elson et al. |
| 2004/0167572 A1 | 8/2004 | Roth et al. |
| 2004/0167575 A1 | 8/2004 | Roby |
| 2004/0186487 A1 | 9/2004 | Klein et al. |
| 2004/0193191 A1 | 9/2004 | Starksen et al. |
| 2004/0193217 A1 | 9/2004 | Lubbers et al. |
| 2004/0193257 A1 | 9/2004 | Wu et al. |
| 2004/0226427 A1 | 11/2004 | Trull et al. |
| 2004/0230223 A1 | 11/2004 | Bonutti et al. |
| 2004/0237736 A1 | 12/2004 | Genova et al. |
| 2004/0254609 A1 | 12/2004 | Esplin |
| 2004/0260340 A1 | 12/2004 | Jacobs et al. |
| 2004/0265282 A1 | 12/2004 | Wright et al. |
| 2004/0267309 A1 | 12/2004 | Garvin |
| 2005/0004601 A1 | 1/2005 | Kong et al. |
| 2005/0004602 A1 | 1/2005 | Hart et al. |
| 2005/0033324 A1 | 2/2005 | Phan |
| 2005/0033367 A1 | 2/2005 | Leung et al. |
| 2005/0034431 A1 | 2/2005 | Dey et al. |
| 2005/0038472 A1 | 2/2005 | Furst |
| 2005/0049636 A1 | 3/2005 | Leiboff |
| 2005/0055051 A1 | 3/2005 | Grafton |
| 2005/0059984 A1 | 3/2005 | Chanduszko et al. |
| 2005/0065533 A1 | 3/2005 | Magen et al. |
| 2005/0070959 A1 | 3/2005 | Cichocki, Jr. |
| 2005/0080455 A1 | 4/2005 | Schmieding et al. |
| 2005/0085857 A1 | 4/2005 | Peterson et al. |
| 2005/0096698 A1 | 5/2005 | Lederman |
| 2005/0106211 A1 | 5/2005 | Nelson et al. |
| 2005/0113936 A1 | 5/2005 | Brustad et al. |
| 2005/0119694 A1 | 6/2005 | Jacobs et al. |
| 2005/0125020 A1 | 6/2005 | Meade et al. |
| 2005/0125034 A1 | 6/2005 | Cichocki, Jr. |
| 2005/0125035 A1 | 6/2005 | Cichocki, Jr. |
| 2005/0149064 A1 | 7/2005 | Peterson et al. |
| 2005/0149118 A1 | 7/2005 | Koyfman et al. |
| 2005/0154255 A1 | 7/2005 | Jacobs |
| 2005/0171561 A1 | 8/2005 | Songer et al. |
| 2005/0177190 A1 | 8/2005 | Zamierowski |
| 2005/0181009 A1 | 8/2005 | Hunter et al. |
| 2005/0182444 A1 | 8/2005 | Peterson et al. |
| 2005/0182445 A1 | 8/2005 | Zamierowski |
| 2005/0186247 A1 | 8/2005 | Hunter et al. |
| 2005/0197699 A1 | 9/2005 | Jacobs et al. |
| 2005/0199249 A1 | 9/2005 | Karram |
| 2005/0203576 A1 | 9/2005 | Sulamanidze et al. |
| 2005/0209542 A1 | 9/2005 | Jacobs et al. |
| 2005/0209612 A1 | 9/2005 | Nakao |
| 2005/0234510 A1 | 10/2005 | Zamierowski |
| 2005/0240220 A1 | 10/2005 | Zamierowski |
| 2005/0267531 A1 | 12/2005 | Ruff et al. |
| 2005/0267532 A1 | 12/2005 | Wu |
| 2005/0277984 A1 | 12/2005 | Long |
| 2005/0283246 A1 | 12/2005 | Cauthen, III et al. |
| 2006/0020272 A1 | 1/2006 | Gildenberg |
| 2006/0030884 A1 | 2/2006 | Young et al. |
| 2006/0036266 A1 | 2/2006 | Sulamanidze et al. |
| 2006/0058470 A1 | 3/2006 | Rizk |
| 2006/0058574 A1 | 3/2006 | Priewe et al. |
| 2006/0058799 A1 | 3/2006 | Elson et al. |
| 2006/0058844 A1 | 3/2006 | White et al. |
| 2006/0063476 A1 | 3/2006 | Dore |
| 2006/0064115 A1 | 3/2006 | Allen et al. |
| 2006/0064116 A1 | 3/2006 | Allen et al. |
| 2006/0064127 A1 | 3/2006 | Fallin et al. |
| 2006/0079469 A1 | 4/2006 | Anderson et al. |
| 2006/0079935 A1 | 4/2006 | Kolster |
| 2006/0085016 A1 | 4/2006 | Eremia |
| 2006/0089525 A1 | 4/2006 | Mamo et al. |
| 2006/0089672 A1 | 4/2006 | Martinek |
| 2006/0111734 A1 | 5/2006 | Kaplan et al. |
| 2006/0111742 A1 | 5/2006 | Kaplan et al. |
| 2006/0116503 A1 | 6/2006 | Lendlein et al. |
| 2006/0122608 A1 | 6/2006 | Fallin et al. |
| 2006/0135994 A1 | 6/2006 | Ruff |
| 2006/0135995 A1 | 6/2006 | Ruff |
| 2006/0140999 A1 | 6/2006 | Lendlein et al. |
| 2006/0142784 A1 | 6/2006 | Kontos |
| 2006/0155328 A1 | 7/2006 | Foerster |
| 2006/0193769 A1 | 8/2006 | Nelson et al. |
| 2006/0194721 A1 | 8/2006 | Allen |
| 2006/0200062 A1 | 9/2006 | Saadat |
| 2006/0207612 A1 | 9/2006 | Jackson et al. |
| 2006/0229671 A1 | 10/2006 | Steiner et al. |
| 2006/0235445 A1 | 10/2006 | Birk et al. |
| 2006/0235447 A1 | 10/2006 | Walshe |
| 2006/0235516 A1 | 10/2006 | Cavazzoni |
| 2006/0241658 A1 | 10/2006 | Cerundolo |
| 2006/0249405 A1 | 11/2006 | Cerwin et al. |
| 2006/0253126 A1 | 11/2006 | Bjerken et al. |
| 2006/0257629 A1 | 11/2006 | Ledlein et al. |
| 2006/0258938 A1 | 11/2006 | Hoffman et al. |
| 2006/0272979 A1 | 12/2006 | Lubbers et al. |
| 2006/0276808 A1 | 12/2006 | Arnal et al. |
| 2006/0282099 A1 | 12/2006 | Stokes et al. |
| 2006/0286289 A1 | 12/2006 | Prajapati et al. |
| 2006/0287675 A1 | 12/2006 | Prajapati et al. |
| 2006/0287676 A1 | 12/2006 | Prajapati et al. |
| 2006/0293710 A1 | 12/2006 | Foerster et al. |
| 2007/0005109 A1 | 1/2007 | Popadiuk et al. |
| 2007/0005110 A1 | 1/2007 | Collier et al. |
| 2007/0016251 A1 | 1/2007 | Roby |
| 2007/0021779 A1 | 1/2007 | Garvin et al. |
| 2007/0027475 A1 | 2/2007 | Pagedas |
| 2007/0038249 A1 | 2/2007 | Kolster |
| 2007/0065663 A1 | 3/2007 | Trull et al. |
| 2007/0088135 A1 | 4/2007 | Lendlein et al. |
| 2007/0088391 A1 | 4/2007 | McAlexander et al. |
| 2007/0134292 A1 | 6/2007 | Suokas et al. |
| 2007/0135840 A1 | 6/2007 | Schmieding |
| 2007/0135843 A1 | 6/2007 | Burkhart |
| 2007/0151961 A1 | 7/2007 | Kleine et al. |
| 2007/0156175 A1 | 7/2007 | Weadock et al. |
| 2007/0167958 A1 | 7/2007 | Sulamanidze et al. |
| 2007/0187861 A1 | 8/2007 | Geneva et al. |
| 2007/0208355 A1 | 9/2007 | Ruff |
| 2007/0208377 A1 | 9/2007 | Kaplan et al. |
| 2007/0213770 A1 | 9/2007 | Dreyfuss |
| 2007/0219587 A1 | 9/2007 | Accardo |
| 2007/0224237 A1 | 9/2007 | Hwang et al. |
| 2007/0225642 A1 | 9/2007 | Houser et al. |
| 2007/0225761 A1 | 9/2007 | Shetty |
| 2007/0225763 A1 | 9/2007 | Zwolinski et al. |
| 2007/0227914 A1 | 10/2007 | Cerwin et al. |
| 2007/0233188 A1 | 10/2007 | Hunt et al. |
| 2007/0239206 A1 | 10/2007 | Shelton, IV et al. |
| 2007/0239207 A1 | 10/2007 | Beramendi |
| 2007/0243228 A1 | 10/2007 | McKay et al. |
| 2007/0257395 A1 | 11/2007 | Lindh et al. |
| 2007/0282247 A1 | 12/2007 | Desai et al. |
| 2007/0293892 A1 | 12/2007 | Takasu |
| 2008/0004490 A1 | 1/2008 | Bosley, Jr. et al. |
| 2008/0004603 A1 | 1/2008 | Larkin et al. |
| 2008/0009838 A1 | 1/2008 | Schena et al. |
| 2008/0009888 A1 | 1/2008 | Ewers et al. |
| 2008/0009902 A1 | 1/2008 | Hunter et al. |
| 2008/0027273 A1 | 1/2008 | Gutterman |
| 2008/0027486 A1 | 1/2008 | Jones et al. |

(56) References Cited

U.S. PATENT DOCUMENTS

| | | |
|---|---|---|
| 2008/0046094 A1 | 2/2008 | Han et al. |
| 2008/0058869 A1 | 3/2008 | Stopek et al. |
| 2008/0064839 A1 | 3/2008 | Hadba et al. |
| 2008/0066764 A1 | 3/2008 | Paraschac et al. |
| 2008/0066765 A1 | 3/2008 | Paraschac et al. |
| 2008/0066766 A1 | 3/2008 | Paraschac et al. |
| 2008/0066767 A1 | 3/2008 | Paraschac et al. |
| 2008/0077181 A1 | 3/2008 | Jones et al. |
| 2008/0082113 A1 | 4/2008 | Bishop et al. |
| 2008/0082129 A1 | 4/2008 | Jones et al. |
| 2008/0086169 A1 | 4/2008 | Jones et al. |
| 2008/0086170 A1 | 4/2008 | Jones et al. |
| 2008/0109036 A1 | 5/2008 | Stopek et al. |
| 2008/0131692 A1 | 6/2008 | Rolland et al. |
| 2008/0132943 A1 | 6/2008 | Maiorino et al. |
| 2008/0169059 A1 | 7/2008 | Messersmith et al. |
| 2008/0195147 A1 | 8/2008 | Stopek |
| 2008/0208358 A1 | 8/2008 | Bellamkonda et al. |
| 2008/0215072 A1 | 9/2008 | Kelly |
| 2008/0221618 A1 | 9/2008 | Chen et al. |
| 2008/0234731 A1 | 9/2008 | Leung et al. |
| 2008/0248216 A1 | 10/2008 | Yeung et al. |
| 2008/0255611 A1 | 10/2008 | Hunter |
| 2008/0262542 A1 | 10/2008 | Sulamanidze et al. |
| 2008/0281338 A1 | 11/2008 | Wohlert et al. |
| 2008/0281355 A1 | 11/2008 | Mayer et al. |
| 2008/0281357 A1 | 11/2008 | Sung et al. |
| 2008/0300491 A1 | 12/2008 | Bonde et al. |
| 2008/0312688 A1 | 12/2008 | Nawrocki et al. |
| 2009/0012560 A1 | 1/2009 | Hunter et al. |
| 2009/0018577 A1 | 1/2009 | Leung et al. |
| 2009/0043336 A1 | 2/2009 | Yuan et al. |
| 2009/0076543 A1 | 3/2009 | Maiorino et al. |
| 2009/0082856 A1 | 3/2009 | Flanagan |
| 2009/0088835 A1 | 4/2009 | Wang |
| 2009/0099597 A1 | 4/2009 | Isse |
| 2009/0105753 A1 | 4/2009 | Greenhalgh et al. |
| 2009/0107965 A1 | 4/2009 | D'Agostino |
| 2009/0112236 A1 | 4/2009 | Stopek |
| 2009/0112259 A1 | 4/2009 | D'Agostino |
| 2009/0143819 A1 | 6/2009 | D'Agostino |
| 2009/0200487 A1 | 8/2009 | Maiorino et al. |
| 2009/0210006 A1 | 8/2009 | Cohen et al. |
| 2009/0216253 A1 | 8/2009 | Bell et al. |
| 2009/0222039 A1 | 9/2009 | Dreyfus et al. |
| 2009/0226500 A1 | 9/2009 | Avelar et al. |
| 2009/0228021 A1 | 9/2009 | Leung |
| 2009/0248066 A1 | 10/2009 | Wilkie |
| 2009/0248067 A1 | 10/2009 | Maiorino |
| 2009/0248070 A1 | 10/2009 | Kosa et al. |
| 2009/0250356 A1 | 10/2009 | Kirsch et al. |
| 2009/0250588 A1 | 10/2009 | Robeson et al. |
| 2009/0259233 A1 | 10/2009 | Bogart et al. |
| 2009/0259251 A1 | 10/2009 | Cohen |
| 2009/0287245 A1 | 11/2009 | Ostrovsky et al. |
| 2009/0299407 A1 | 12/2009 | Yuan et al. |
| 2009/0299408 A1 | 12/2009 | Schuldt-Hempe et al. |
| 2009/0306710 A1 | 12/2009 | Lindh et al. |
| 2009/0312791 A1 | 12/2009 | Lindh, Sr. et al. |
| 2009/0318958 A1 | 12/2009 | Ochiai |
| 2010/0021516 A1 | 1/2010 | McKay |
| 2010/0023055 A1 | 1/2010 | Rousseau |
| 2010/0030261 A1 | 2/2010 | McCalin |
| 2010/0057123 A1 | 3/2010 | D'Agostino et al. |
| 2010/0063540 A1 | 3/2010 | Maiorino |
| 2010/0071833 A1 | 3/2010 | Maiorino |
| 2010/0087855 A1 | 4/2010 | Leung et al. |
| 2010/0101707 A1 | 4/2010 | Maiorino et al. |
| 2010/0140115 A1 | 6/2010 | Kirsch |
| 2010/0146770 A1 | 6/2010 | Morency et al. |
| 2010/0160961 A1 | 6/2010 | Nawrocki et al. |
| 2010/0163056 A1 | 7/2010 | Tschopp et al. |
| 2010/0211097 A1 | 8/2010 | Hadba et al. |
| 2010/0211098 A1 | 8/2010 | Hadba et al. |
| 2010/0230300 A1 | 9/2010 | Hunter et al. |
| 2010/0239635 A1 | 9/2010 | McClain et al. |
| 2010/0292718 A1 | 11/2010 | Sholev et al. |
| 2010/0294103 A1 | 11/2010 | Genova et al. |
| 2010/0294104 A1 | 11/2010 | Genova et al. |
| 2010/0294105 A1 | 11/2010 | Genova et al. |
| 2010/0294106 A1 | 11/2010 | Genova et al. |
| 2010/0294107 A1 | 11/2010 | Genova et al. |
| 2010/0298637 A1 | 11/2010 | Ruff |
| 2010/0298639 A1 | 11/2010 | Leung et al. |
| 2010/0298848 A1 | 11/2010 | Leung et al. |
| 2010/0298867 A1 | 11/2010 | Ruff |
| 2010/0298868 A1 | 11/2010 | Ruff |
| 2010/0298871 A1 | 11/2010 | Ruff et al. |
| 2010/0298874 A1 | 11/2010 | Leung et al. |
| 2010/0298875 A1 | 11/2010 | Leung et al. |
| 2010/0298876 A1 | 11/2010 | Leung et al. |
| 2010/0298878 A1 | 11/2010 | Leung et al. |
| 2010/0298879 A1 | 11/2010 | Leung et al. |
| 2010/0298880 A1 | 11/2010 | Leung et al. |
| 2010/0313723 A1 | 12/2010 | Genova et al. |
| 2010/0313729 A1 | 12/2010 | Genova et al. |
| 2010/0313730 A1 | 12/2010 | Genova et al. |
| 2010/0318122 A1 | 12/2010 | Leung et al. |
| 2010/0318123 A1 | 12/2010 | Leung et al. |
| 2010/0318124 A1 | 12/2010 | Leung et al. |
| 2011/0009902 A1 | 1/2011 | Leung et al. |
| 2011/0022086 A1 | 1/2011 | D'Agostino et al. |
| 2011/0046668 A1 | 2/2011 | Goraltchouk et al. |
| 2011/0046669 A1 | 2/2011 | Goraltchouk et al. |
| 2011/0093010 A1 | 4/2011 | Genova et al. |
| 2011/0106152 A1 | 5/2011 | Kozlowski |
| 2011/0125188 A1 | 5/2011 | Goraltchouk et al. |
| 2011/0130774 A1 | 6/2011 | Criscuolo et al. |
| 2011/0166597 A1 | 7/2011 | Herrmann et al. |
| 2011/0251640 A1 | 10/2011 | Lauria |
| 2011/0264138 A1 | 10/2011 | Avelar et al. |
| 2011/0288583 A1 | 11/2011 | Goraltchouk et al. |
| 2011/0319932 A1 | 12/2011 | Avelar et al. |
| 2012/0101522 A1 | 4/2012 | Megaro et al. |
| 2012/0109188 A1 | 5/2012 | Viola |
| 2012/0116449 A1 | 5/2012 | Kirsch et al. |
| 2012/0245629 A1 | 9/2012 | Gross et al. |
| 2012/0245659 A1 | 9/2012 | Matthews |
| 2013/0072971 A1 | 3/2013 | Kim et al. |
| 2013/0103078 A1 | 4/2013 | Longo et al. |
| 2013/0165971 A1 | 6/2013 | Leung et al. |
| 2013/0172931 A1 | 7/2013 | Gross et al. |
| 2013/0180966 A1 | 7/2013 | Gross et al. |
| 2013/0204295 A1 | 8/2013 | Hunter et al. |
| 2013/0226233 A1 | 8/2013 | D'Agostino et al. |
| 2013/0226234 A1 | 8/2013 | Avelar et al. |
| 2013/0238021 A1 | 9/2013 | Gross et al. |
| 2013/0238022 A1 | 9/2013 | Gross et al. |
| 2013/0245684 A1 | 9/2013 | Ruff et al. |
| 2013/0317545 A1 | 11/2013 | Gross et al. |
| 2013/0345745 A1 | 12/2013 | Kim |
| 2014/0039527 A1 | 2/2014 | Avelar et al. |

FOREIGN PATENT DOCUMENTS

| | | |
|---|---|---|
| CN | 2640420 | 9/2004 |
| DE | 01810800 | 6/1970 |
| DE | 03227984 | 2/1984 |
| DE | 04302895 | 8/1994 |
| DE | 19618891 | 4/1997 |
| DE | 19833703 | 2/2000 |
| DE | 10245025 | 4/2004 |
| DE | 102005004317 | 6/2006 |
| EP | 0121362 | 9/1987 |
| EP | 0329787 | 8/1989 |
| EP | 0513713 | 5/1992 |
| EP | 0428253 | 7/1994 |
| EP | 0632999 | 1/1995 |
| EP | 0513736 | 2/1995 |
| EP | 0464479 | 3/1995 |
| EP | 0464480 | 3/1995 |
| EP | 0576337 A1 | 3/1997 |
| EP | 0576337 B1 | 3/1997 |
| EP | 0574707 | 8/1997 |

(56) References Cited

FOREIGN PATENT DOCUMENTS

| | | |
|---|---|---|
| EP | 0612504 | 11/1997 |
| EP | 0558993 | 4/1998 |
| EP | 0913123 | 5/1999 |
| EP | 0916310 | 5/1999 |
| EP | 0664198 | 6/1999 |
| EP | 0960600 | 12/1999 |
| EP | 0705567 | 3/2002 |
| EP | 0673624 | 8/2002 |
| EP | 0839499 | 9/2003 |
| EP | 0755656 | 12/2003 |
| EP | 1075843 | 2/2005 |
| EP | 1525851 | 4/2005 |
| EP | 1532942 | 5/2005 |
| EP | 0826337 | 12/2005 |
| EP | 0991359 | 11/2007 |
| EP | 1852071 | 11/2007 |
| EP | 2036502 | 3/2009 |
| EP | 1948261 | 11/2010 |
| EP | 2245992 | 11/2010 |
| EP | 1726317 | 7/2012 |
| EP | 2338421 | 11/2012 |
| FR | 2619129 | 2/1989 |
| FR | 2693108 | 1/1994 |
| FR | 2926452 | 3/2011 |
| GB | 0267007 | 3/1927 |
| GB | 1091282 | 11/1967 |
| GB | 1428560 | 7/1973 |
| GB | 1506362 | 4/1978 |
| GB | 1508627 | 4/1978 |
| JP | 47-044390 | 11/1972 |
| JP | 1506362 | 4/1978 |
| JP | 54-116419 | 9/1979 |
| JP | 63-288146 | 11/1988 |
| JP | 64-013034 | 1/1989 |
| JP | 001113091 | 5/1989 |
| JP | 3-080868 | 4/1991 |
| JP | 3-165751 | 7/1991 |
| JP | 4-096758 | 3/1992 |
| JP | 4-266749 | 9/1992 |
| JP | 6-134028 | 5/1994 |
| JP | 9-103477 | 4/1997 |
| JP | 410085225 | 4/1998 |
| JP | 10-337291 | 12/1998 |
| JP | 11-313826 | 11/1999 |
| JP | 011332828 | 12/1999 |
| JP | 2002-059235 | 2/2002 |
| JP | 2003-275217 | 9/2003 |
| JP | 2006-522656 | 10/2006 |
| JP | 2007-502281 | 2/2007 |
| JP | 2007-537017 | 12/2007 |
| JP | 2009-118967 | 6/2009 |
| JP | 2009-247889 | 10/2009 |
| JP | 2009-247900 | 10/2009 |
| JP | 2010-063892 | 3/2010 |
| KR | 10-2005-0072908 A | 7/2005 |
| KR | 6013299 | 2/2006 |
| NZ | 501224 | 3/2002 |
| NZ | 531262 | 12/2005 |
| RU | 2139690 | 10/1999 |
| RU | 2175855 | 11/2001 |
| RU | 2241389 | 12/2004 |
| RU | 2268752 | 1/2006 |
| RU | 2318458 | 3/2008 |
| SU | 560599 | 6/1977 |
| SU | 1745214 | 7/1992 |
| SU | 1752358 | 8/1992 |
| WO | WO 96/06565 | 3/1966 |
| WO | WO 86/00020 | 1/1986 |
| WO | WO 87/01270 | 3/1987 |
| WO | WO 88/09157 | 12/1988 |
| WO | WO 89/05618 | 6/1989 |
| WO | WO 90/09149 | 8/1990 |
| WO | WO 90/14795 | 12/1990 |
| WO | WO 92/22336 | 12/1992 |
| WO | WO 95/16399 | 6/1995 |
| WO | WO 95/29637 | 11/1995 |
| WO | WO 97/00047 | 1/1997 |
| WO | WO 98/52473 | 11/1998 |
| WO | WO 98/55031 | 12/1998 |
| WO | WO 99/21488 | 5/1999 |
| WO | WO 99/33401 | 7/1999 |
| WO | WO 99/52478 | 10/1999 |
| WO | WO 99/59477 | 11/1999 |
| WO | WO 99/62431 | 12/1999 |
| WO | WO 00/51658 | 9/2000 |
| WO | WO 00/51685 | 9/2000 |
| WO | WO 01/06952 | 2/2001 |
| WO | WO 01/56626 | 8/2001 |
| WO | WO 03/001979 | 1/2003 |
| WO | WO 03/003925 | 1/2003 |
| WO | WO 03/017850 | 3/2003 |
| WO | WO 03/045255 | 6/2003 |
| WO | WO 03/077772 | 9/2003 |
| WO | WO 03/092758 | 11/2003 |
| WO | WO 03/103733 | 12/2003 |
| WO | WO 03/103972 | 12/2003 |
| WO | WO 03/105703 | 12/2003 |
| WO | WO 2004/014236 | 2/2004 |
| WO | WO 2004/030517 | 4/2004 |
| WO | WO 2004/030520 | 4/2004 |
| WO | WO 2004/030704 | 4/2004 |
| WO | WO 2004/030705 | 4/2004 |
| WO | WO 2004/062459 | 7/2004 |
| WO | WO 2004/100801 | 11/2004 |
| WO | WO 2004/112853 | 12/2004 |
| WO | WO 2005/016176 | 2/2005 |
| WO | WO 2005/074913 | 8/2005 |
| WO | WO 2005/096955 | 10/2005 |
| WO | WO 2005/096956 | 10/2005 |
| WO | WO 2005/112787 | 12/2005 |
| WO | WO 2006/005144 | 1/2006 |
| WO | WO 2006/012128 | 2/2006 |
| WO | WO 2006/037399 | 4/2006 |
| WO | WO 2006/061868 | 6/2006 |
| WO | WO 2006/079469 | 8/2006 |
| WO | WO 2006/082060 | 8/2006 |
| WO | WO 2006/099703 | 9/2006 |
| WO | WO 2006/138300 | 12/2006 |
| WO | WO 2007/005291 | 1/2007 |
| WO | WO 2007/005296 | 1/2007 |
| WO | WO 2007/038837 | 4/2007 |
| WO | WO 2007/053812 | 5/2007 |
| WO | WO 2007/089864 | 8/2007 |
| WO | WO 2007/112024 | 10/2007 |
| WO | WO 2007/133103 | 11/2007 |
| WO | WO 2007/145614 | 12/2007 |
| WO | WO 2008/107919 | 9/2008 |
| WO | WO 2008/128113 | 10/2008 |
| WO | WO 2008/136549 | 11/2008 |
| WO | WO 2009/042841 | 4/2009 |
| WO | WO 2009/068252 | 6/2009 |
| WO | WO 2009/086172 | 7/2009 |
| WO | WO 2009/087105 | 7/2009 |
| WO | WO 2009/097556 | 7/2009 |
| WO | WO 2009/151876 | 8/2009 |
| WO | WO 2010/052007 | 12/2009 |
| WO | WO 2010/008815 | 1/2010 |
| WO | WO 2011/053375 | 5/2010 |
| WO | WO 2011/025760 | 3/2011 |
| WO | WO 2011/139916 | 5/2011 |
| WO | WO 2011/140283 | 11/2011 |
| WO | WO 2015/069042 | 5/2015 |

OTHER PUBLICATIONS

US 6,503,260, (withdrawn)
Bacci, Pier Antonio, "Chirurgia Estetica Mini Invasiva Con Fili Di Sostegno", Collana di Arti, Pensiero e Scienza; Minelli Editore-2006; 54 pgs.
Behl, Marc et al., "Shape-Memory Polymers", Materials Today Apr. 2007; 10(4); 20-28.

(56) References Cited

OTHER PUBLICATIONS

Belkas, J. S. et al., "Peripheral nerve regeneration through a synthetic hydrogel nerve tube", Restorative Neurology and Neuroscience 23 (2005) 19-29.

Bellin, I. et al., "Polymeric triple-shape materials", Proceedings of the National Academy of Sciences of the United States of America Nov. 28, 2006; 2103(48):18043-18047.

Boenisch, U.W. et al 'Pull-Out strength and stiffness of meniscal repair using absorbable arrows or Ti-Cron vertical and horizontal loop sutures' American Journal of Sports Medicine, Sep.-Oct. 1999 vol. 27, Issue 5, pp. 626-631.

Buckley, P.R. 'Actuation of Shape Memory Polymer using Magnetic Fields for Applications in Medical Devices' Master of Science in Mechanical Engineering in Massachusetts Institute of Technology Jun. 2003, 144 pages.

Buncke, Jr., H.J. et al 'The Suture Repair of One-Millimeter Vessels, microvascular surgery' (1966) Report of First Conference; Oct. 6-7 pp. 24-35.

Bunnell, S. 'Gig pull-out suture for tendons' J Bone Joint Surg. Am (1954) vol. 36A, No. 4 pp. 850-851.

CCPR Centro De Cirurgia Plastica e Reabilitacao 'Up Lifting (Aptos Threads) http://ccpr.com.br/up1-1.htm, Aug. 19, 2002 pp. 1-2.

Dahlin, Lars, "Techniques of Peripheral Nerve Repair", Scandinavian Journal of Surgery 97: 310-316, 2008.

Datillo, Jr., P.P. 'Knotless Bi-directional Barbed Absorbable Surgical Suture' Dissertation submitted to the Graduate Faculty of North Carolina State University Textile Management and Technology Nov. 2002, 75 pages.

Datillo, Jr. P.P. et al 'Medical Textiles: Application of an Absorbable Barbed Bi-Directional Surgical Suture' (2002) The Journal of Textile and Apparel Technology and Management vol. 2, Issue 2, pp. 1-5.

Datillo, Jr., P. et al 'Tissue holding performance of knotless absorbable sutures' Society for Biomaterials 29th Annual Meeting Transactions (2003) p. 101.

Declaration of Dr. Gregory L. Ruff, dated Aug. 19, 2005, 8 pages, with Exhibits A-E.

De Persia, Raúl et al., "Mechanics of Biomaterials: Sutures After the Surgery", Applications of Engineering Mechanics in Medicine, GED-University of Puerto Rico, Mayaguez May 2005, p. F1-F27.

Delorenzi, C.L., "Barbed Sutures: Rationale and Technique", Aesthetic Surg. J. Mar. 2006 26(2): 223-229.

Demyttenaere, Sebastian V. et al., "Barbed Suture for Gastrointestinal Closure: A Randomized Control Trial", Surgical Innovation; vol. 16, No. 3; Sep. 2009; pp. 237-242.

Einarsson, Jon I. et al., "Barbed Suture, now in the toolbox of minimally invasive gyn surgery", OBG Management; vol. 21, No. 9; Sep. 2009; pp. 39-41.

Gross, Alex, "Physician perspective on thread lifts", Dermatology Times Feb. 2006 27(2): 2 pages.

Gross, R.A. et al 'Biodegradable Polymers for the Environment' Science (2002) vol. 297, Issue 5582 pp. 803.

Han, H. et al 'Mating and Piercing Micromechanical Suture for Surface Bonding Applications' (1991) Proceedings of the 1991 Micro Electro Mechanical Systems (MEMS>91), An Investigation of Micro Structures, Sensors, Actuators, Machines and Robots pp. 253-258.

Ingle, N.P. et al 'Barbed Suture Anchoring Strength: Applicability to Dissimilar Polymeric Materials' College of Textiles, North Carolina State University, 7th World Biomaterials Congress 2004, 1 page.

Ingle, N.P. et al 'Mechanical Performance and Finite Element Analysis of Bi-directional Barbed Sutures' Master of Science in Textile Technology & Management at North Carolina State University Aug. 2003, 126 pages.

Ingle, N.P. et al., "Optimizing the tissue anchoring performance of barbed sutures in skin and tendon tissues", Journal of Biomechanics 43 (2010); pp. 302-309.

Ingle, Nilesh P et al., "Testing the Tissue-holding Capacity of Barbed Sutures", College of Textiles, North Carolina State University, Fiber Science, The Next Generation Oct. 17-19, 2005, New Jersey Institute of Technology, Newark, NJ, 4 pages.

Jennings et al 'A New Technique in primary tendon repair' Surg. Gynecol. Obstet. (1952) vol. 95, No. 5 pp. 597-600.

Jeong, H.E. et al 'A nontransferring dry adhesive with hierarchial polymer nanohairs' PNAS 106 (14) pp. 5639-5644 (2009).

Kaminer, M. et al., "ContourLift™: A New Method of Minimally Invasive Facial Rejuvenation", Cosmetic Dermatology Jan. 2007; 20(1): 29-35.

Kelch et al., "Shape-memory Polymer Networks from Olio [(∈-hydroxycaproate)-co-glycolate]dimethacrylates and Butyl Acrylate with Adjustable Hydrolytic Degradation Rate", Biomacromolecules 2007;8(3):1018-1027.

Khademhosseini, Ali et al., "Nanobiotechnology Drug Delivery and Tissue Engineering", Chemical Engineering Progress 102:38-42 (2006).

Kuniholm J.F. et al 'Automated Knot Tying for Fixation in Minimally Invasive, Robot Assisted Cardiac Surgery' Master of Science in Mechanical & Aerospace Engineering at North Carolina State University May 2003, 71 pages.

Lendlein, A. et al 'Biodegradable, Elastic Shape-Memory Polymers for Potential Biomedical Applications' (2002) Science vol. 296 pp. 1673-1676.

Lendlein, A. et al 'Shape-Memory Polymers' Agnew Chem. Int. Ed. (2002) vol. 41 pp. 2034-2057.

Leung, J. et al 'Barbed, Bi-directional Medical Sutures: Biomechanical Properties and Wound Closure Efficacy Study' 2002 Society for Biomaterials 28th Annual Meeting Transactions 1 page.

Leung, J. et al 'Barbed, Bi-directional Surgical Sutures' International Conference & Exhibition on Healthcare & Medical Textiles, Jul. 8-9, 2003 pp. 1-8.

Leung, J. et al 'Barbed, Bi-directional Surgical Sutures: In Vivo Strength and Histopathology Evaluations' 2003 Society for Biomaterials 29th Annual Meeting Transactions pp. 100.

Leung, J. et al., "Barbed Suture Technology: Recent Advances", Medical Textiles 2004, Advances in Biomedical Textiles and Healthcare Products, Conference Proceedings, IFAI Expo 2004, Oct. 26-27, 2004, Pittsburgh, PA., pp. 62-80.

Leung, J. et al 'Performance Enhancement of a Knotless Suture via Barb Geometry Modifications' 7th World Biomaterials Congress 2004, 1 page.

Li, Y.Y. et al 'Polymer Replicas of Photonic Porous Silicon for Sensing and Drug Delivery Applications' (2003) Science vol. 299 pp. 2045-2047.

Liu, Changdeng et al., "Shape Memory Polymer with Improved Shape Recovery", Mater. Res. Soc. Symp. Proc. vol. 855E, 2005 Materials Research Society, pp. W4.7.1-W4.7.6.

Madduri, Srinivas, et al., "Neurotrophic factors release from nerve conduits for peripheral axonal regeneration", European Cells and Materials vol. 16; Suppl. 1 (2008), p. 14.

Madhave et al 'A biodegradable and biocompatible gecko-inspired tissue adhesive' PNAS 105(7) pp. 2307-2312 (2008).

Maitland et al., "Prototype laser-activated shape memory polymer foam device for embolic treatment of aneurysms", Journal of Biomedical Optics May/Jun. 2007;12(3): pp. 030504-1 to 030504-3.

Malina, M. et al 'Endovascular AAA Exclusion: Will Stents with Hooks and Barbs Prevent Stent-Graft Migration' Journal Endovascular Surgery (1998) vol. 5 pp. 310-317.

Mansberger et al 'A New Type Pull-Out Wire for Tendon Surgery: A Preliminary Report' Department of Surgery, University Hospital and University of Maryland School of Medicine, Baltimore, Maryland, Received for Publication May 10, 1951 pp. 119-121.

Martin, D.P. et al 'Medical applications of poly-4-hydroxybutyrate: a strong flexible absorbable biomaterial' Biochemical Engineering Journal vol. 16 (2003) pp. 97-105.

Mason, M.L. 'Primary and Secondary Tendon Suture. A discussion of the significance of technique in tendon surgery' (1940) Surg Gynecol Obstet 70.

(56) References Cited

OTHER PUBLICATIONS

McKee, GK 'Metal anastomosis tubes in tendon suture' The Lancet (1945) pp. 659-660.
McKenzie 'An Experimental Multiple Barbed Suture for the Long Flexor Tendons of the Palm and Fingers' The Journal of Bone and Joint Surgery (1967) vol. 49B, No. 3 pp. 440-447.
Middleton and Tipton 'Synthetic Biodegradable Polymers as Medical Devices' (1998) Medical Plastics and Biomaterials Magazine, 9 pages.
Moran et al., "Bidirectional-Barbed Sutured Knotless Running Anastomosis v Classic van Velthovan in a Model System", Journal of Endourology Oct. 2007; 21(10); 1175-1177.
Mullner, "Metal Foam Has a Good Memory", Dec. 18, 2007 Original story at <http://www.physorg.com/news117214996.html>.
Murtha et al., "Evaluation of a Novel Technique for Wound Closure Using a Barbed Suture", Journal of the American Society of Plastic Surgeons 2006; 117(6); 1769-1780.
Nie, Zhihong and Kumacheva, Eugenia, "Patterning surfaces with functional polymers", Nature Materials vol. 7(2008): 277-290.
Paul, Malcolm D., "Bidirectional Barbed Sutures for Wound Closure: Evolution and Applications", Journal of the American College of Certified Wound Specialists (2009) 1, 51-57.
Paul, Malcolm D. and Rui Avelar, "Quill™ SRS Techniques & Procedures a Novel Approach to Soft Tissue Approximation", Canada, Angiotech Pharmaceuticals, Inc., First Edition Aug. 2007: 20 pages.
Paul, Malcolm D. and Rui Avelar, "Quill™ SRS Techniques & Procedures a Novel Approach to Soft Tissue Approximation", Canada, Angiotech Pharmaceuticals, Inc., Second Edition Aug. 2008: 20 pages.
Paul, Malcolm D. and Rui Avelar, "Quill™ SRS Techniques & Procedures a Novel Approach to Soft Tissue Approximation", Canada, Angiotech Pharmaceuticals, Inc., Third Edition 2009, Aug. 2007-2009: 27 pages.
Paul, Malcolm D. and Rui Avelar, "Quill™ SRS Techniques & Procedures a Novel Approach to Soft Tissue Approximation", Canada, Angiotech Pharmaceuticals, Inc., Fourth Edition 2010, Aug. 2007-2010: 27 pages.
Paul, Malcolm D., "Using Barbed Sutures in Open/Subperiosteal Midface Lifting", Aesthetic Surgery Journal 2006(26): 725-732.
Potenza, A. 'Tendon Healing Within the Flexor Digital Sheath in the Dog: An Experimental Study' Journal of Bone & Joint Surgery (1962) vol. 44A No. 1 pp. 49-64.
Pulvertaft 'Suture Materials and Tendon Junctures' American Journal of Surgery (1965) vol. 109 pp. 346-352.
Quill Medical, Inc. 'Barbed Sutures, wrinkle filters give patients more innovative, non-surgical options' Press Release of Program presented at American Society of Plastic Surgeons annual scientific meeting; Philadelphia, Oct. 9, 2004 3 pages.
Quill Medical, Inc. 'Quill Medical's Novel-Self-Anchoring Surgical Suture Approved for Sale in Europe' Press Release; Research Triangle Park, N.C. May 10, 2004, 1 page.
Quill Medical, Inc., "Quill Medical, Inc. Receives FDA Clearance for First-in-Class Knot-Less Self-Anchoring Surgical Suture", Press Release; Research Triangle Park, N.C., Nov. 4, 2004, 1 page.
Richert, Ludovic, et al., "Surface Nanopatterning to Control Cell Growth", Advanced Materials 2008(15): 1-5.
Rodeheaver, G.T. et al., "Barbed Sutures for Wound Closure: In Vivo Wound Security, Tissue Compatibility and Cosmesis Measurements", Society for Biomaterials 30th Annual Meeting Transactions, 2005, 2 pages.
Rofin-Baasel 'Laser Marking on Plastic Materials' (2001) RB50.0, Rofin-Baasel Inc. 2 pages.
Ruff, Gregory, "Technique and Uses for Absorbable Barbed Sutures", Aesthetic Surgery Journal Sep./Oct. 2006; 26:620-628.
Scherman, Peter et al., "Sutures as longitudinal guides for the repair of nerve defects-Influence of suture numbers and reconstruction of nerve bifurcations", Restorative Neurology and Neuroscience 23 (2005) 79-85.
Schmid A. et al 'The outspreading anchor cord. A material for arthroscopic suturing of a fresh anterior cruciate ligament rupture' Surgical Clinic of the University of Gottingen (1987) pp. 417-426.
Semenov, G.M. et al 'Surgical Suture' (2001) Piter, Saint Petersburg, pp. 12-13 and 92-98.
Serafetinides, AA 'Short pulse laser beam interactions with polymers biocompatible materials and tissue' Proce SPIE vol. 3052 (1996) pp. 111-123.
Sulamanidze, M. et al., "Aptos Suture Lifting Methods: 10 Years of Experience", Clin Plastic Surg 36 (2009); pp. 281-306.
Sulamanidze, M.A. et al 'Clinical aspects of bloodless facelift using APTOS filaments' A.V. Vishnevsky Institute of Surgery, Bol'shaya Serpukhovskaya ul, 7, 113811, Moscow, Russia (2002) pp. 24-34.
Sulamanidze, M.A. et al 'Facial lifting with Aptos threads' International Journal of Cosmetic Surgery and Aesthetic Dermatology (2001) No. 4 pp. 1-8.
Sulamanidze, M.A. et al 'Management of Facial Rhytids by Subcutaneous Soft Tissue Dissection' (2000) International Journal of Cosmetic Surgery and Aesthetic Dermatology vol. 2 No. 4 pp. 255-259.
Sulamanidze, M.A. et al 'Morphological foundations of facelift using Aptos filaments' Bolshaya Serpukhovskaya ul 27, 113811 Moscow, Russia (2002) pp. 19-26.
Sulamanidze, M.A. et al 'Removal of Facial Soft Tissue Ptosis with Special Threads' Dermatol Surg (2002) vol. 28 pp. 367-371.
Sulamanidze, MD, M.A., et al., "Soft tissue lifting in the mid-face: old philosophy, new approach-internal stitching technique (Aptos Needle)", Plastic and Aesthetic Surgery Clinic Total Sharm, Moscow, Russia, (2005):15-29.
Sulzle, Inc. B.G. et al Drilled End Surgical Needles Jul. 2002 Syracuse, New York.
Surgical Specialties Corporation, "Wound Closure Catalog"; Summer 2005, 5 pages.
Szarmach, R. et al 'An Expanded Surgical Suture and Needle Evaluation and Selection Program by a Healthcare Resource Management Group Purchasing Organization' Journal of Long-Term Effects of Medical Implants (2003) vol. 13 No. 3 pp. 155-170.
Tan E.L. et al., "A wireless, passive strain sensor based on the harmonic response of magnetically soft materials", Smart Materials and Structures 17 (2008): pp. 1-6.
Verdan, C. 'Primary Repair of Flexor Tendons' Journal of Bone and Joint Surgery (1960) vol. 42, No. 4 pp. 647-657.
Villa, Mark T. et al., "Barbed Sutures: A Review of Literature", Plastic and Reconstructive Surgery; Mar. 2008; vol. 121, No. 3; pp. 102e-108e.
Wu. W. 'Barbed Sutures in Facial Rejuvenation' Aesthetic Surgery Journal (2004) vol. 24 pp. 582-587.
Zoltan, J. 'Cicatrix Optimia: Techniques for Ideal Wound Healing' English language edition University Park Press Baltimore (1977) Chapter 3 pp. 54-55.
Croce, E. et al 'Intracorporeal Knot-Tying and Suturing Techniques in Laparoscopic Survery: Technical Details' Journal of the Society of Laparoendoscopic Surgeons (2000) vol. 4 pp. 17-22.
International Search Report for PCT/US2008/077813 dated Mar. 31, 2009.

\* cited by examiner

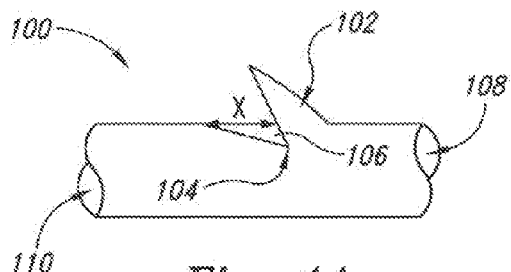
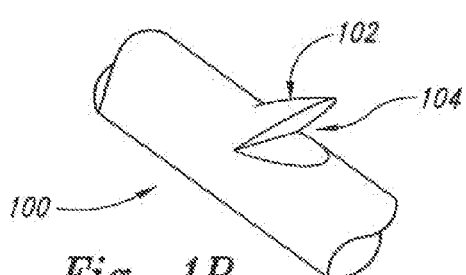
Fig. 1A
Prior Art
Fig. 1B
Prior Art
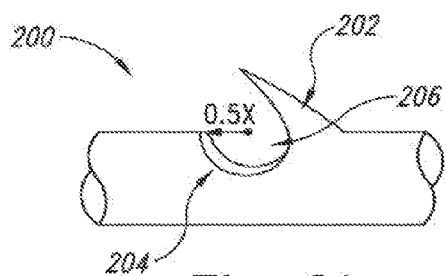
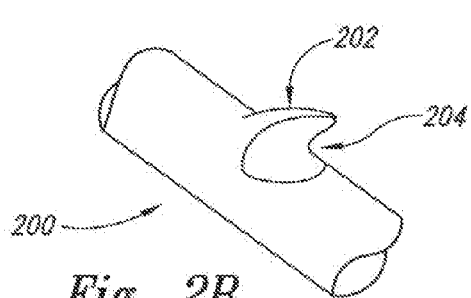
Fig. 2A
Fig. 2B
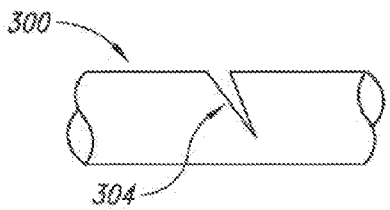
Fig. 3
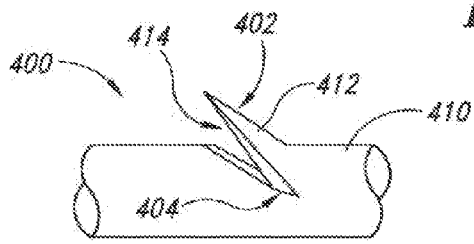
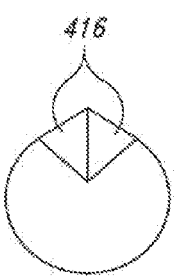
Fig. 4A
Fig. 4B
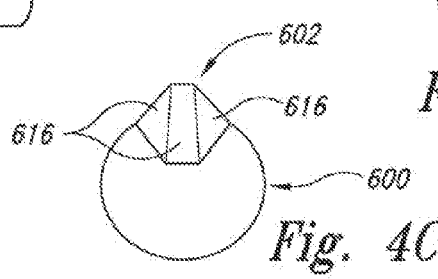
Fig. 4C

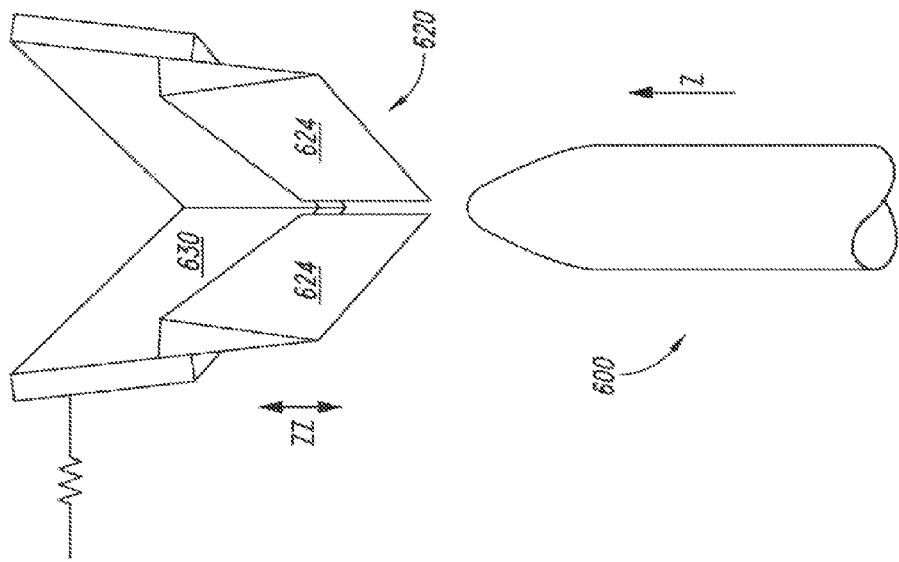
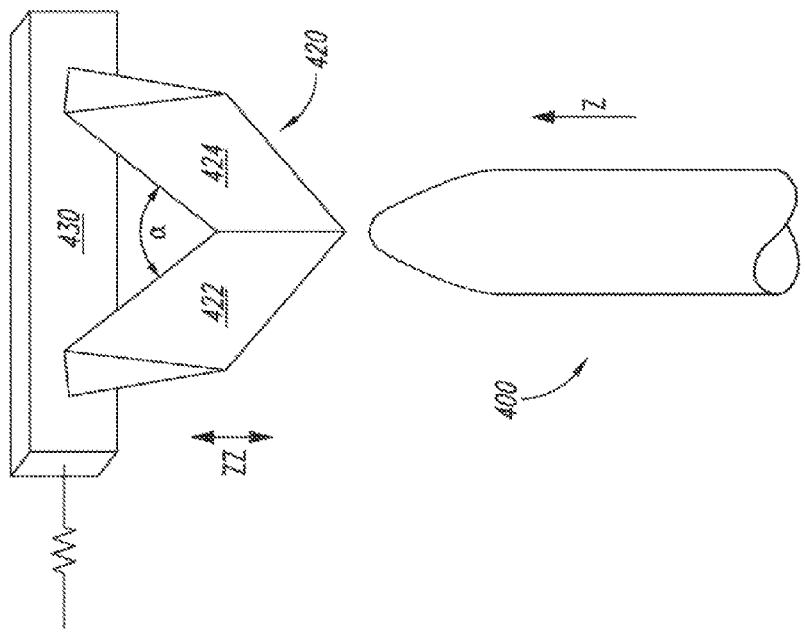

SELF-RETAINING SUTURES INCLUDING TISSUE RETAINERS HAVING IMPROVED STRENGTH

CROSS-REFERENCE TO RELATED APPLICATIONS

This application is a divisional of U.S. application Ser. No. 12/680,176, filed Mar. 25, 2010, which is a national phase of International Application No. PCT/US2008/077813, filed Sep. 26, 2008, which claims benefit of priority of U.S. Provisional Application No. 60/975,758, filed Sep. 27, 2007. The complete disclosures of the aforementioned related U.S. patent applications are hereby incorporated herein by reference for all purposes.

TECHNICAL FIELD

The present invention relates generally to methods and devices for joining or positioning bodily tissue in surgical and cosmetic applications.

BACKGROUND

Sutures are commonly used for closing or binding together wounds in human or animal tissue, such as skin, muscles, tendons, internal organs, nerves, and blood vessels. Sutures can be formed from non-absorbable material such as silk, nylon, polypropylene, or cotton, or alternatively sutures can be formed from bio-absorbable material such as, but not limited to, homopolymers and/or copolymers of glycolide, lactide, p-dioxanone and ε-caprolactone.

A suture can include retainers protruding from the suture periphery and arranged to allow passage of the self-retaining suture when drawn in one direction (with respect to the direction of protrusion of the retainer) through tissue but resist movement of the self-retaining suture when drawn in the opposite direction. Retainers can reduce slippage of the suture at least in a direction along the suture and can optionally obviate knotting of the suture.

Single-directional self-retaining sutures can include an end that is pointed to allow penetration and passage through tissue when drawn by the end and an opposite end that includes an anchor for engaging tissue at the initial insertion point to limit movement of the suture. Alternatively, bi-directional self-retaining sutures can include retainers grouped and extending in one direction along one portion of the suture and opposing retainers grouped and extending in an opposing direction along another portion of the suture. When implanted so that both groups of retainers are engaging tissue, the retainers can resist movement of the suture through tissue in either direction.

A surgeon may use a surgical needle with an attached suture (which can be a smooth monofilament or can be a multi-filament) to pierce the tissue alternately on opposing faces of a wound to sew the wound closed. Techniques for placement of self-retaining sutures in tissue to close or bind together wounds can include threading the self-retaining suture in straight-line patterns such as zig-zag, and curvi-linear patterns such as alpha, sinusoidal, and corkscrew. A surgeon may also use self-retaining sutures to position and support tissue where there is no wound in procedures such as cosmetic surgery of the face, neck, abdominal or thoracic region among others.

BRIEF SUMMARY OF THE INVENTION

Briefly stated, the present invention provides sutures, methods of forming retainers in a suture, systems useful to form a retainer in a suture, and related technology.

Within one aspect of the present invention, a suture is provided, the suture being useful in a procedure applied to tissue, where the suture comprises: an elongated body having a first end and a second end; and a plurality of retainers arranged along a portion of the elongated body; wherein the retainers substantially yield to motion of the elongated body within the tissue when the elongated body is drawn in a first direction and resist motion of the elongated within the tissue when the elongated body is drawn in a second direction opposite the first direction; and wherein the retainers include an upper surface and a lower surface, the upper surface extending from a periphery of the elongated body and the lower surface having at least two facets. Within various optional embodiments, which may be combined or not, (a) one or both of the elongated body and the plurality of retainers includes an associated material to be delivered to the tissue, where optionally, the associated material is one or more of a hormone, a drug, and medicine; (b) the plurality of retainers is a first set and the portion of the elongated body is a first portion; and further comprising: a second set including a plurality of retainers arranged along a second portion of the elongated body; wherein the retainers substantially yield to motion of the elongated body within the tissue when the elongated body is drawn at the second end and resist motion of the elongated within the tissue when the elongated body is drawn at the first end; and wherein the retainers of the second set include an upper surface and a lower surface, the upper surface extending from a periphery of the elongated body and the lower surface having at least two facets.

Within another aspect, the present invention provides a method of forming one or more retainers in a suture having an elongated body with a first end and a second end for use in a surgical procedure applied to tissue, where the method comprises: positioning the elongated body; oscillating a cutting edge so that the cutting edge alternately penetrates the elongated body and exits the elongated body, wherein the cutting edge includes a first blade and a second blade arranged to form an angle; wherein the cutting edge forms one or more retainers so that the one or more retainers substantially yield to motion of the elongated body within the tissue when the elongated body is drawn at the first end and resist motion of the elongated within the tissue when the elongated body is drawn at the second end. Within various optional embodiments, which may be combined for not, (a) the method further comprises heating the cutting edge so that the one or more retainers are annealed, where optionally the cutting edge is heated to approximately 200° C.; (b) the first blade and the second blade as used in the method comprise sapphire.

Within another aspect, the present invention provides a suture for use in a procedure applied to tissue, where the suture comprises: an elongated body having a first end and a second end; and a plurality of retainers arranged along a portion of the elongated body; wherein the retainers substantially yield to motion of the elongated body within the tissue when the elongated body is drawn at the first end and resist motion of the elongated within the tissue when the elongated body is drawn at the second end; and wherein the retainers include an upper surface and a lower surface formed by a cutting edge, the upper surface extending from a periphery of the elongated body and the lower surface joining the elongated body at an apex having a radius of curvature larger than a radius of curvature of the cutting edge. Within various optional embodiments, which may be combined or not, (a) one or both of the elongated body and the plurality of retainers includes an associated material to be delivered to the tissue, where optionally the associated material is one or more of a hormone, a drug, and medicine; (b) the radius of curvature of the apex is up to 0.5 times the retainer channel opening length; (c) the radius of curvature of the apex is 0.1 to 0.25 times the retainer channel opening length; (d) the plurality of retainers is a first set, the portion of the elongated body is a first portion, and the cutting edge is a first cutting edge; and further comprising: a second set including a plurality of retainers arranged along a second portion of the elongated body; wherein the retainers substantially yield to motion of the elongated body within the tissue when the elongated body is drawn at the second end and resist motion of the elongated within the tissue when the elongated body is drawn at the first end; and wherein the retainers of the second set include an upper surface and a lower surface defined by a second cutting edge, the upper surface extending from a periphery of the elongated body and the lower surface joining the elongated body at an apex having a radius of curvature larger than a radius of curvature of the second cutting edge.

Within another aspect, the present invention provides a method of forming one or more retainers in a suture for use in a surgical procedure applied to tissue comprising: positioning an elongated body having a first end and a second end; heating a cutting edge to a temperature that distorts the elongated body; and oscillating the cutting edge so that the cutting edge alternately penetrates the elongated body and exits the elongated body; wherein the cutting edge forms the one or more retainers so that the one or more retainers substantially yield to motion of the elongated body within the tissue when the elongated body is drawn at the first end and resist motion of the elongated within the tissue when the elongated body is drawn at the second end; and wherein the cutting edge forms the one or more retainers to include an upper surface and a lower surface defined by a cutting edge, the upper surface extending from a periphery of the elongated body and the lower surface joining the elongated body at an apex having a radius of curvature larger than a radius of curvature of the cutting edge. In various optional embodiments, which may be combined, (a) the method further comprises annealing the one or more retainers with the cutting edge, optionally wherein the one or more retainers are annealed by heating the cutting edge within the range of 100-250° C.; (b) the radius of curvature of the apex is up to 0.5 times the retainer channel opening length, for example, the radius of curvature of the apex is 0.1 to 0.25 times the retainer channel opening length; and (c) the lower surface is one of V-shaped, rectangular-shaped, and trapezoidal-shaped.

Within another aspect, the present invention provides a system to form a retainer in a suture for use in a procedure applied to tissue, the system comprising: a cutting edge including a first blade and a second blade arranged at an angle relative to the first blade; a mechanism to oscillate the cutting edge; and a heater connected with the cutting edge to heat the cutting edge. In various optional embodiments, which may be combined, (a) the first blade and the second blade are sapphire blades; (b) the first blade and the second blade are one of metallic blades and ceramic blades; (c) the first blade and the second blade are substantially in contact and the second blade is arranged at 90° relative to the first blade; (d) the heater is a copper plate that conducts heat to the cutting edge; (e) the mechanism to oscillate the cutting edge is a cam.

Within another aspect, the present invention provides a suture for use in a procedure applied to tissue, where the suture comprises: an elongated body having a first end and a second end; and a plurality of retainers arranged along a portion of the elongated body; wherein the retainers substantially yield to motion of the elongated body within the tissue when the elongated body is drawn at the first end and resist motion of the elongated within the tissue when the elongated body is drawn at the second end; and wherein the retainers include an upper surface and a lower surface formed by a cutting edge, and wherein the upper surface includes a supplementary material formed on at least a portion of the upper surface. In various optional embodiments, which may be combined, (a) the supplementary material is deposited by a printing technique; (b) the supplementary material has substantially the same material properties as the elongated body; (c) the supplementary material has one or both of higher yield strength and higher Young's Modulus than the elongated body.

Within another aspect, the present invention provides a suture for use in a procedure applied to tissue, where the suture comprises: an elongated body having a first end and a second end; and a plurality of retainers arranged along a portion of the elongated body; wherein the retainers substantially yield to motion of the elongated body within the tissue when the elongated body is drawn at the first end and resist motion of the elongated within the tissue when the elongated body is drawn at the second end; and wherein a spacing distance is formed between retainers arranged at a position along a circumference of the elongated body, the spacing distance being a function of the tissue strength and composition.

The details of one or more embodiments are set forth in the description below. Other features, objects and advantages will be apparent from the description, the drawings, and the claims. In addition, the disclosures of all patents and patent application referenced herein are incorporated by reference in their entirety.

BRIEF DESCRIPTION OF THE DRAWINGS

Further details of the present invention are explained with the help of the attached drawings in which:

FIG. 1A is a side view of a suture in accordance with the prior art including a retainer protruding generally at an angle in a direction along an axis of the suture.

FIG. 1B is a perspective view of the suture of FIG. 1A.

FIG. 2A is a side view of an embodiment of a suture including a retainer wherein an apex of a cut forming the retainer is enlarged to distribute applied stress applied across a larger surface, reducing concentration of the stress.

FIG. 2B is a perspective view of the suture of FIG. 2A.

FIG. 3 is a side view of an improperly formed retainer.

FIG. 4A is a side view of an embodiment of a suture including a retainer wherein the retainer has a lower surface having two converging faces.

FIG. 4B is a front view of the embodiment of FIG. 4A.

FIG. 4C is a front view of an alternative embodiment of a suture including a retainer wherein the retainer has a lower surface having three facets, where adjacent facets are converging.

FIG. 5A top perspective view of a blade configuration for forming the retainer of the suture of FIGS. 4A and 4B.

FIG. 5B top perspective view of a blade configuration for forming the retainer of the suture of FIG. 4C.

DETAILED DESCRIPTION

Figure 6A:
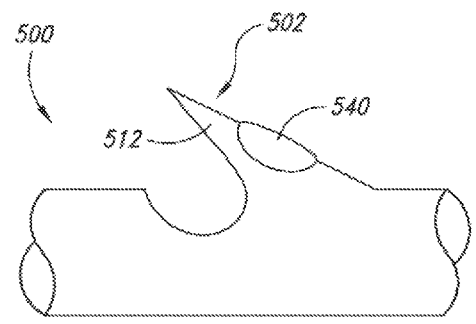
FIG. 6A is a side view of an alternative embodiment of a suture including a retainer with material added to a surface of the retainer.

Self-retaining sutures used in surgical techniques such as wound closure and tissue positioning can provide improved results where the retainers of the sutures provide increased resistance to movement opposite the path of insertion (also referred to hereinafter as "pull-out strength"). Pull-out strength can vary with factors such as retainer geometry, relative positioning of the retainers along the suture, the type of tissue into which the suture is implanted, the surgical or cosmetic technique applied for implantation of the suture, the strength of the core suture, and application for which the suture is used. For example, suture performance may be identified with reference to tissue type, with different sutures being qualified for use in surgical procedures targeting specific tissue. Different tissues will accept favorably different configurations, spacing, and geometries of the retainers. Suturing muscle in an abdomen, for example, can be substantially different from sewing fatty tissue or skin tissue. Sutures can be labeled to identify appropriate procedures and tissue.

Self-retaining suture refers to a suture that may not require a knot in order to maintain its position into which it is deployed during a surgical procedure. Such self-retaining sutures generally include a retaining element or tissue retainer.

Tissue retainer refers to a suture element having a retainer body projecting from the suture body and a retainer end adapted to penetrate tissue. Each retainer is adapted to resist movement of the suture in a direction other than the direction in which the suture is deployed into the tissue by the surgeon, by being oriented to substantially face the deployment direction (i.e. the retainers lie flat when pulled in the deployment direction; and open or "fan out" when pulled in a direction contrary to the deployment direction). As the tissue-penetrating end of each retainer faces away from the deployment direction when moving through tissue during deployment, the tissue retainers should generally avoid catching or grabbing tissue during this phase. Once the self-retaining suture has been deployed, a force exerted in another direction (often substantially opposite to the deployment direction) causes the retainers to be displaced from their deployment positions (i.e. resting substantially along the suture body), forces the retainer ends to open (or "fan out") from the suture body in a manner that catches and penetrates into the surrounding tissue, and results in tissue being caught between the retainer and the suture body; thereby "anchoring" or affixing the self retaining suture in place. By way of example only, tissue retainer or retainers can include hooks, projections, barbs, darts, extensions, bulges, anchors, protuberances, spurs, bumps, points, cogs, tissue engagers, tractions means, surface roughness, surface irregularities, surface defects, edges, facets and the like.

FIG. 1A is a side view and FIG. 1B is a perspective view of a suture 100 in accordance with the prior art including a retainer 102 protruding from a periphery of the suture 100. Retainers can have myriad geometric shapes, for example pyramidal and conical. The retainer 102 is formed when a cutting edge (not shown) is brought into contact with the suture 100 so that the cutting edge 102 penetrates the periphery of the suture 100. The cutting edge forms a wedge cut 106 having an apex 104 at a termination point of the cutting edge's penetration. The retainer 102 is urged apart from the suture 100 so that the retainer 102 is gapped to form a retainer channel opening x from the periphery of the suture 100 from which the retainer 102 is separated. The apex 104 likely includes a small radius of curvature defined largely by a rounding of the cutting edge. For example, the cutting edge may be a knife blade including rounding inherent in a structure subjected to abrasion forces, or for example the cutting edge may be a wire having a circular cross-section with a diameter. It can be desirable for the cutting edge to have an extremely small radius of curvature (i.e., to be a sharp as practicable) so that the periphery of the suture is penetrated cleanly. The extremely small rounding of the cutting edge results in a sharp apex 104, which produces an unfavorably high stress concentration.

In a common surgical or cosmetic procedure, the suture of FIGS. 1A and 1B may be threaded or otherwise inserted into tissue and drawn in the direction of a first end 108. The force of the tissue pressing against the suture 100 causes the retainer 102 to substantially collapse and yield to movement of the suture through the tissue. If the suture 100 is drawn in the direction of a second, opposite end 110, the edge of the retainer 102 grabs the tissue and resists movement. Additional force applied to the suture 100 can increase the retainer channel opening x, causing a high stress concentration at the apex 104. This results in an increased probability of fracture initiation and propagation at the apex resulting in suture failure.

Referring to FIGS. 2A and 2B, an embodiment of a self-retaining suture 200 in accordance with the present invention can include a retainer 202 formed by a cut 206 with an apex 204 radius of curvature larger than a radius of curvature of the cutting blade (not shown). In a preferred embodiment, the radius of curvature of the apex 204 can range from 0.1 to 0.25 times the retainer channel opening x, although in other embodiments the radius of curvature of the apex 204 can be smaller than 0.1x or larger than 0.25×(e.g., 0.5x). Stress reduction at the apex of the cut can be achieved by increasing a radius of curvature at the apex 204 of the cut 206. Embodiments of methods in accordance with the present invention can be applied to form sutures within the periphery of the suture have an apex larger than the cutting blade. Alternatively, the apex geometry can be non-circular (i.e. the groove terminating in a flat face, a multi-faced facet, or any other given geometric shape or combination thereof).

In an embodiment of a method, a heated cutting edge such as a blade or wire can penetrate the periphery of the suture, heating the suture material as the knife cuts. The temperature and contact time can be varied to achieve the most desirable curvature of the apex. Preferably, the cutting edge can be heated to a temperature between the melting temperature of the suture material and the decomposition temperature of the suture material. For example, polyethylene terephthalate can have a melting temperature of about 260° C. and a decomposition temperature of about 350° C., some polyglycolic acid homopolymers can have a melting temperature of about 180° C. and a decomposition temperature of about 225° C., some types of nylon can have a melting temperature of about 250° C. and a decomposition temperature of about 375° C., and polydioxanone can have a melting temperature of about 90° C. and a decomposition temperature of about 175° C. It should be noted that these temperature characteristics are exemplary, and melting and decomposition temperatures may vary within a class of materials. For example, nylon melting and decomposition temperatures can vary substantially based on the chemical composition.

In an alternative embodiment of a method of increasing the radius of curvature of the apex, a first cutting edge can form the retainer (and cut), and a second heated edge or blunt heated dye can be subsequently positioned within the cut. A still further embodiment of a method of increasing the radius of curvature of the apex can comprise a two-step cut, whereby a first cutting edge (e.g., a knife blade or wire) having an edge with a first radius of curvature penetrates the periphery of the suture to cause a cut, followed by a second cutting edge having an edge with a second, larger radius of curvature to widen the apex of the cut. The temperature, radius of curvature of the dye, pressure applied during forming and contact time can be varied to achieve the most desirable curvature.

A common technique for forming retainers on sutures includes feeding or drawing the suture across a pulley (also called an anvil). As the suture twists, a cutting edge slices across the suture, forming retainers. Twisting the suture may or may not affect the mechanical properties of the suture along an unaltered periphery of the suture and/or at the retainer. In an alternative embodiment, a method of forming a suture including retainers having a cut with a radius of curvature larger than a cutting edge can include feeding or drawing a suture from a feed spool to a take-up spool that are spinning at a matched angular velocity. A cutting edge is heated to a temperature sufficient to melt a material with which the suture is formed, and the cutting edge is rotated across the surface of the suture to form the retainers. The cutting edge can be heated by any known technique for heating small precision tools, to a temperature sufficient to cause a desired melting of the suture material without causing undesired stretching, mechanical deformation or excessive diameter reduction. For example, a conductive blade or wire can be heated by resistive heating to a temperature of approximately 200 degrees C. Alternatively, where achievable, one or both of the cutting edge and the suture can be heated by a laser, directed gas, flame or torch so that when the cutting edge penetrates the suture to form a retainer, a local temperature near the apex of the cut is sufficient to achieve a desired geometric result. Where a laser is used to heat the suture, a polymer or copolymer comprising the suture can be doped to absorb the wavelengths of the laser. The area to which the heating source is directed can be as small as 10 nanometers across.

Referring to FIG. 3, a cut 304 caused by a cutting edge with intent to form a retainer is shown that is generally non-protruding from the periphery of the suture 300. Such a result can occur where a material has insufficient plasticity and is predominantly deformed in the elastic region during retainer cutting. A retainer formed in such a material will tend to lay flat rather than "stand up" by protruding from the periphery. A retainer that fails to protrude from the periphery is less likely to catch the tissue in which it is arranged. Mechanical properties of the specific suture material are considered in order to form a retainer geometry having preferred characteristics. A retainer formed in a material having undesirably high elasticity can have an improved protrusion from the periphery of the suture by annealing the local suture material at least at the base of a retainer site. Annealing the base of the retainer causes polymer chains to realign themselves and relieves internal stresses in a polymer. During cutting, these residual stresses may cause the retainers to lay flat. Relieving the residual stresses at the base of the retainer by annealing can allow the retainers to protrude from the periphery of the suture.

To anneal a polymer, the polymer is heated to a temperature above some crystallization temperature for an amount of time to change its microstructure, and then cooled at a given rate to retain or obtain a different microstructure. For example, the crystallization temperature for polydioxanone is about 40° C., while a crystallization temperature for a copolymer of glycolide ∈-caprolactone in a 72/28 ratio is about 75° C. Sutures are typically formed from extruded polymer and are annealed after extrusion to relieve some of the alignment of polymer chains, to recover some elongation, and to drive out residual solvents. The sutures can subsequently be heated in an oven over a period of time to sterilize the sutures. Some annealing can occur during sterilization; although where sutures are sterilized using techniques employing relatively low temperatures (such as sterilization by ethylene oxide) the annealing is typically not effective in reducing internal stresses. The semi-crystalline structure that results from processing provides a suture with mixed properties including high yield strength and acceptable malleability.

In a preferred embodiment, annealing of the cut retainer is achieved by local heating of the retainer at the base of the retainer while the retainer is protruding to a generally desired degree. Local heating of the retainer can be achieved (as described above with reference to increasing a radius of curvature of the apex) by heating the cutting edge to a sufficient temperature. As mentioned above, a cutting edge can be heated by resistive heating, or by other conductive or convective means. Alternatively, the retainer can be heated by heated gas (such as hot nitrogen gas), a flame, a torch or some other heat source. It is proposed that heating with a cutting edge at a sufficient temperature (e.g., 200 degrees C.) for 4-5 milliseconds, and cooling by ambient temperature, can result in a sufficiently protruding retainer. Alternatively, the retainer can be actively cooled. For example, a Peltier device is a device for electrically controlling temperature that can be miniaturized to suit small features.

Referring to FIGS. 4A and 4B, an alternative embodiment of a self-retaining suture 400 in accordance with the present invention can include a retainer 402 with an upper surface 412 extending from a periphery 410 of the elongated body and a lower surface 414 having at least two facets 416. As seen in the front view of FIG. 4B, the retainer can have a roughly pie-slice (i.e., wedge) shape. The increased cross-section moment of inertia (also known as the second moment of area) of the retainer improves strength, and can improve resistance to the tendency of a retainer to fold back on itself and yield to movement of the suture through the tissue, as described above. This retainer further reduces stress concentrations along the lower surface of the retainer and the suture when compared with the retainers of FIG. 1A. The retainer need not be shaped as a perfect wedge, but rather preferably has at least two facets to improve resistance to back bending. Thus, for example in FIGS. 4C and 5B, a suture 600 is shown having a retainer 602 having a roughly trapezoidal shape, with three facets 616.

Referring to FIG. 5A, an embodiment of a method of forming a retainer 402 in a suture 400 such as shown in FIGS. 4A and 4B is illustrated. A V-shape cutting edge 420 can be formed arranging two blades 422,424 in proximity to form a desired cutting angle α and resembling a V. Preferably, the blades 422,424 can be placed close to each other at a cutting angle α of 90°, although the blades 422,424 can be arranged to form an obtuse or acute angle where desired. The cutting edge 420 can optionally be heated to provide local heating to the base of the retainer 402 while cutting the suture 400, thereby annealing the base of the retainer 402 and/or increasing a radius of curvature at apex 404 or the interface of the lower surface 414 of the retainer 402 and the suture 400. In a preferred embodiment, the cutting edge 420 can comprise sapphire blades. Sapphire blades are ceramic blades typically having an edge radius one or two magnitudes lower than an edge radius of a steel blade. Further, sapphire blades generally maintain their mechanical characteristics over the temperature ranges desirable for annealing polymer and co-polymer materials. Maintaining mechanical characteristics (i.e., geometry of a cut produced) can be desired where the retainers are extremely small and therefore sensitive to small changes. Further, sapphire blades are more abrasion resistant than, for example, typical steel blades, providing more repeatable results over long term use. Further, sapphire blades can be sharpened more effectively than steel blades. In another embodiment of this invention the V-shaped blade can have any of its surfaces be convex or concave to allow for the selection of an appropriate final retainer design, either maximizing the moment of inertia of the retainer or the remaining cross sectional area of the suture.

In an embodiment, the suture 400 can be spooled or otherwise fed or drawn in a direction z after extrusion at a generally constant speed, in a non-twisting path. For manufacturing a one-direction retainer suture, a cutting edge 420 can be arranged in each of four quadrants of a circle. The cutting edge 420 can comprise the sapphire blades that oscillate in a direction z so that the cutting edge 420 alternately penetrates the suture 420 and pulls away from a cut. As mentioned, the cutting edge 420 is heated to both cut and anneal the retainer 402 simultaneously, causing the retainer 402 to protrude from the periphery of the suture 400. The cutting edge can be oscillated by a cam device, for example.

To heat the cutting edge 420, the sapphire blades can be mounted or otherwise place in conductive communication with a copper heating plate 430. The copper plate 430 can heat the cutting edge 420 through conduction to a temperature above the crystallization temperature of the suture material. For example, where the suture material is a copolymer of glycolide ϵ-caprolactone the cutting edge can be heated to about 200° C. The temperature of the cutting edge can be maintained in a temperature range to provide satisfactory results. The cutting edge 420 is generally in conductive proximity to the retainer 402 for generally from four to five milliseconds. In this embodiment, heating the retainer at 200° C. for four to five milliseconds is sufficient to anneal the base of the retainer so that the retainer protrudes from the periphery of the suture. It may be desirable to cause sufficient contact to melt the suture at the apex, thereby increasing a radius of curvature of the apex. The retainers are cooled by the ambient conditions of the environment (generally room temperature) or through directed cooling to provide a desired degree of strand alignment (crystallinity) in the material. Alternatively, the sapphire blades can be heated by a laser beam directed through the sapphire blades. An efficiency of this technique can depend on the absorption of the suture material.

Referring to FIG. 5B, a cutting edge 620 includes two sapphire blades 624 having some finite distance between the cutting surfaces, resulting in a suture 600 having a retainer 602 resembling the retainer 602 of FIG. 4B. Further, an alternative heating plate 630 is shown contacting the surface of the blades 624 rather than contacting the back edge of the blades 624.

For manufacturing a two-direction retainer suture, a cutting edge can be arranged in each of four quadrants of a circle in each of two directions of protrusion/penetration, resulting in eight cutting edges. The cutting edge can comprise the sapphire blades that oscillate so that the cutting edge alternately penetrates the suture and pulls away from the cut. As mentioned, the cutting edge is optionally heated to both cut and anneal the retainer simultaneously, causing the retainer to protrude from the periphery of the suture.

In other embodiments of methods of forming retainers in sutures in accordance with the present invention, other retainer arrangements can be produced. For example, a cutting edge can be arranged in each of three zones to form retainers extending from three circumferential locations along the suture. Alternatively, one or more cutting edges can be rotated so that the retainers are arranged in a helical fashion along the suture. Retainer patterns can be formed to suit a surgical or cosmetic procedure or application, and the properties of the material at the location of the procedure or application.

Figure 6B:
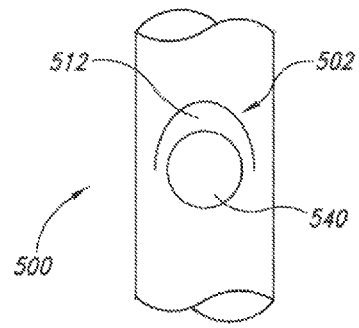
FIG. 6B is a top view of the suture of FIG. 6A including a retainer with material added to a surface of the retainer.

Referring to FIGS. 6A and 6B, a still further embodiment of a self-retaining suture 500 in accordance with the present invention can include a retainer 502 having supplementary material 540 on an upper surface 512 of the retainer 502. The supplementary material 540 can increase the mass of the retainer 502 to improve strength and improve resistance to the tendency of the retainer 502 to fold back on itself and yield to movement of the suture 500 through the tissue, as described above. The supplementary material 540 can comprise a polymer or copolymer that is the same material used to form the suture 502, or a polymer or copolymer material different from the material used to form the suture 500. Alternatively, the supplementary material 540 can be some other material (preferably biocompatible with the tissue in which it is implanted) that can be made to adhere to the upper surface 512 of the retainer 500. Such materials can include metals, ceramics, polymers, composites, or a combination thereof. Preferably, the supplementary material can comprise a material that is stiffer and stronger than the material with which the suture is formed (i.e., the material can have an increased Young's modulus and/or an increased yield strength and ultimate tensile strength). The supplementary material 540 can be formed or deposited before the cutting edge forms the retainer 502 or alternatively the supplementary material 540 can be formed subsequent to forming the protruding retainer 502; however, the supplementary material 540 is generally confined to the surface of the retainer 502. Preferably the supplementary material 540 increases a mean thickness of the retainer up to twice the thickness of the retainer without the supplementary material.

In an embodiment, a printer can used to precisely deposit the supplementary material 540 on the location where the retainer 502 is or will be formed. The printer can be, for example, a dot matrix style printer having a wire or pin that runs back and forth along the suture and prints by impact, striking the location where the retainer is or will be formed to cause the supplementary material to be deposited. Alternatively, some other printing technique can be applied, such as techniques resembling inkjet printing techniques. In still other embodiments, the supplementary material can be deposited or formed using some technique other than printing, such as brush coating, spray coating, selective dip coating, curtain coating, etc.

It is noted that embodiments of sutures in accordance with the present invention can further be impregnated, coated, or otherwise associated with medicine, hormones, drugs, etc., to deliver the associated material to the surgical location. Such associated treatments can be released as the suture material is absorbed into the body. For example, polydioxanone (specifically poly(p-dioxanone)) is a biopolymer that loses most of its strength within six to eight weeks and begins to absorb in about three to four months, and is therefore a longer-term degradable. Polyglycolide and ε-caprolactone, which are degraded primarily by hydrolysis, dissolve generally in a shorter timeframe than polydioxanone. In such embodiments, the associated material can assist in healing wounds closed with the sutures, or alternatively, the suture itself can serve primarily as a vehicle for delivering the associated material over a period of bio-absorption.

Figure 7A:
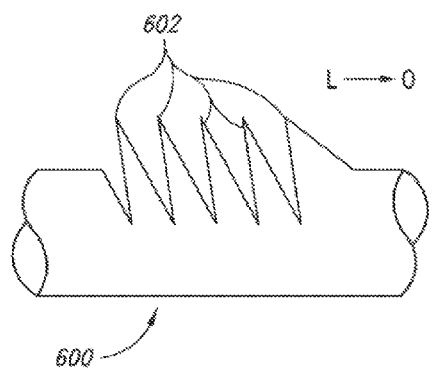
FIG. 7A is a side view of a suture including a plurality of retainers protruding from approximately the same tangent along a periphery of the suture, and spaced so that the retainers overlap a preceding retainer or are overlapped by a subsequent retainer along the suture.
Figure 7B:
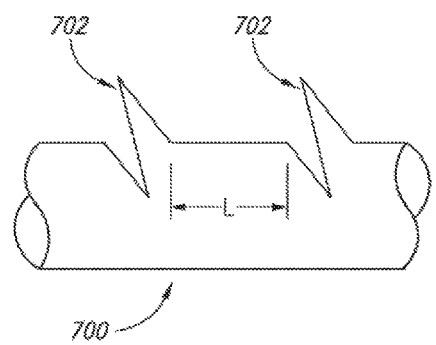
FIG. 7B is a side view of a suture including a pair of retainers protruding from approximately the same tangent along a periphery of the suture. The pair of retainers is spaced a distance along the suture.
Figure 7C:
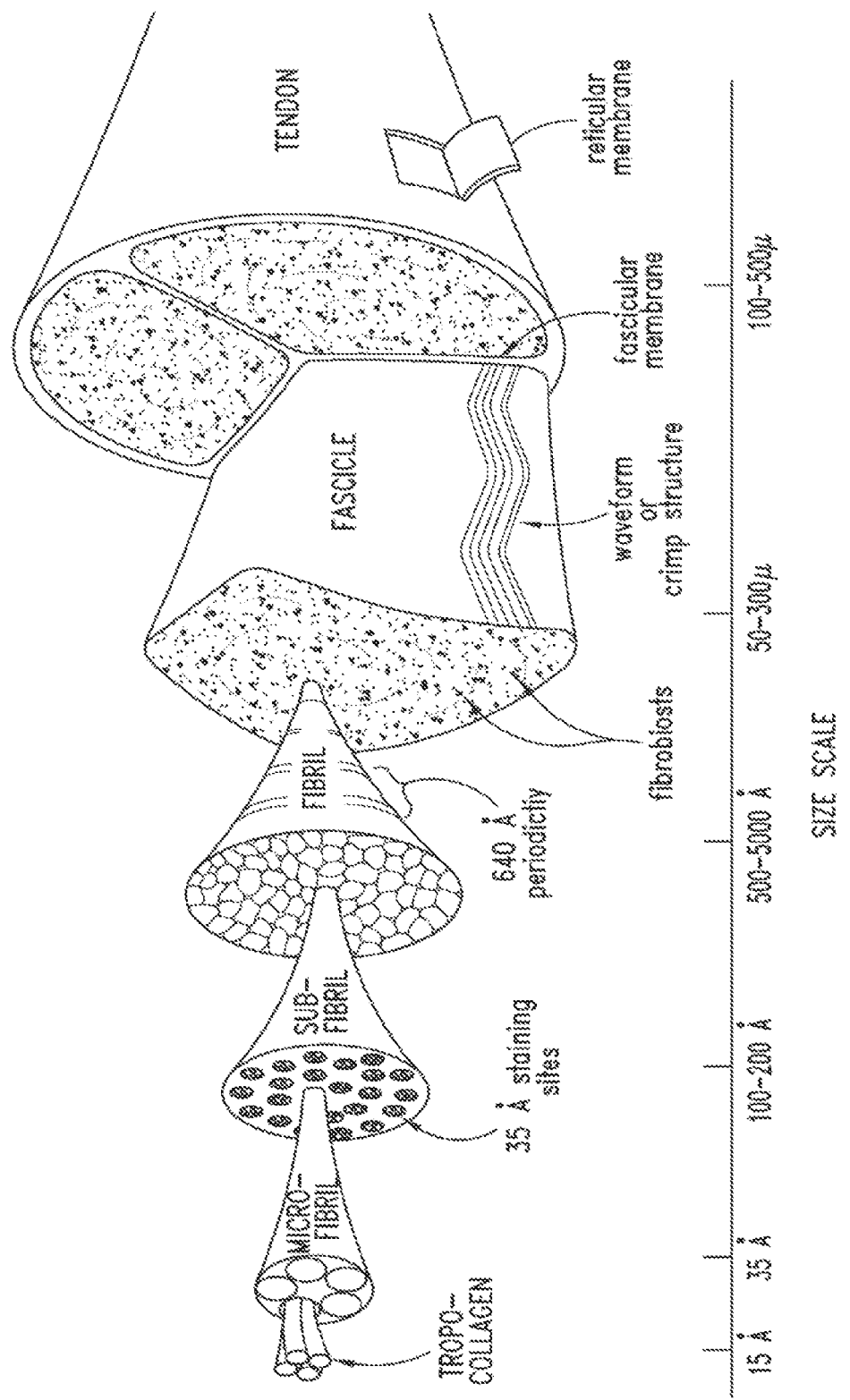
FIG. 7C is an exploded diagram illustrating relative size of tissue and related structures.

FIG. 7A is a side view of a suture 600 including a plurality of retainers 602 protruding from approximately the same tangent along a periphery of the suture 600, and spaced so that the retainers overlap a preceding retainer 602 or overlapped by a subsequent retainer 602 along the suture 600. FIG. 7B is a side view of a suture 700 including a pair of retainers 702 protruding from approximately the same position along the circumference of the suture, the pair of retainers 702 spaced a distance, L, along the suture 700. As the retainers 700 are arranged closer together (i.e., L is reduced) so that the retainers approach a point of overlapping (as shown in FIG. 7A), the target location of the surgical or cosmetic procedure can begin to "see" the retainers as a continuous surface, so that the retainers fail to grab or interfere with suture movement through the target location in a direction opposite the direction of insertion. The degree of overlap or proximity that results in undesirable retainer performance can vary depending on tissue type. Referring to FIG. 7C, for example, when retainers grab or interfere with suture movement through muscle, the retainer commonly grabs or interferes with bundles of muscle, rather than microfibers. On the other hand, when retainers grab or interfere with suture movement through collagen, the retainers typically grab or interfere with collagen fibers (collagen fibrils are tropocollagens packed into an organized overlapping bundle, while collagen fibers are bundles of fibrils). Collagen fibers can have diameters approaching 10 μm. An acceptable proximity or overlap of retainers can generally be proportional to the size of the structure in which the retainers are placed, so that closely arranged retainers are generally acceptable for tissue and structure comprised of microfibers or other small structures, for example. Generally, longer spacing between retainers (i.e., where distance L is large) is appropriate for tissues with relatively larger structures that can support the retainer. In addition, the distance between retainers L can be a function of the strength of the tissue. Overall, a stronger tissue can accommodate a larger retainer distance L and a weaker tissue can accommodate a shorter retainer distance L. Another way to view the dependence of the distance L on the tissue is that a length of tissue equal to L resists the hold of a single retainer. Failure can occur either if the retainer or the tissue opposing the retainer fails. If the distance between retainers L is increasingly small the force which the tissue can withstand also becomes small, whereas if the distance between retainers L is increasingly large the force that the tissue can withstand is excessively large. An equilibrium case L would be such that the force that the tissue (length L) can withstand is equal to the force it takes to bend back or break off the retainer. This distance L is a function of the type of tissue where the suture is used. As such, this translates into the amount of retainers per length of suture being optimized for each particular type of tissue.

The foregoing description of the present invention has been presented for purposes of illustration and description. It is not intended to be exhaustive or to limit the invention to the precise forms disclosed. Many modifications and variations will be apparent to practitioners skilled in this art. The embodiments were chosen and described in order to best explain the principles of the invention and its practical application, thereby enabling others skilled in the art to understand the invention for various embodiments and with various modifications as are suited to the particular use contemplated. It is intended that the scope of the invention be defined by the following claims and their equivalents.

The invention claimed is:

1. A method of forming one or more retainers in a suture having an elongated body with a first end and a second end for use in a surgical procedure applied to tissue comprising:
    positioning the elongated body;
    oscillating a heated cutting edge so that the heated cutting edge alternately penetrates the elongated body and exits the elongated body, wherein the heated cutting edge includes a first blade and a second blade arranged to form an angle;
    wherein the heated cutting edge forms the one or more retainers so that the one or more retainers substantially yield to motion of the elongated body within the tissue when the elongated body is drawn at the first end and resist motion of the elongated body within the tissue when the elongated body is drawn at the second end, and wherein said one or more retainers are annealed with the heated cutting edge.

2. The method of claim 1, wherein the cutting edge is heated to approximately 200° C.

3. The method of claim 1, wherein the first blade and the second blade comprise sapphire.

* * * * *